(12) United States Patent
Volkar et al.

(10) Patent No.: US 11,430,558 B2
(45) Date of Patent: Aug. 30, 2022

(54) SYSTEM, METHOD, AND COMPUTER PROGRAM PRODUCT FOR PEER EXCHANGE OF DATA BETWEEN INJECTION SYSTEMS

(71) Applicant: BAYER HEALTHCARE LLC, Whippany, NJ (US)

(72) Inventors: John Volkar, Valencia, PA (US); Corey Kemper, Pittsburgh, PA (US); Srikanth Mruthik, Parsippany, NJ (US); Michael Oklejewski, Wexford, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 93 days.

(21) Appl. No.: 16/621,018

(22) PCT Filed: Jul. 3, 2018

(86) PCT No.: PCT/US2018/040817
§ 371 (c)(1),
(2) Date: Dec. 10, 2019

(87) PCT Pub. No.: WO2019/010243
PCT Pub. Date: Jan. 10, 2019

(65) Prior Publication Data
US 2020/0202994 A1 Jun. 25, 2020

Related U.S. Application Data

(60) Provisional application No. 62/529,605, filed on Jul. 7, 2017.

(51) Int. Cl.
*G16H 20/17* (2018.01)

(52) U.S. Cl.
CPC .................. *G16H 20/17* (2018.01)

(58) Field of Classification Search
CPC ....................................................... G16H 20/17
(Continued)

(56) References Cited

U.S. PATENT DOCUMENTS 5,713,856 A 2/1998 Eggers et al.
6,162,198 A 12/2000 Coffey et al.
(Continued)

FOREIGN PATENT DOCUMENTS

JP 2002177238 A 6/2002
JP 2003052660 A 2/2003
(Continued)

OTHER PUBLICATIONS

Abdallah, Mohamed Nur; Percutaneous Medical Devices; McGill University (Canada). ProQuest Dissertations Publishing, 2017. 28250249. (Year: 2017).*
(Continued)

*Primary Examiner* — Hiep V Nguyen
(74) *Attorney, Agent, or Firm* — James R. Stevenson; Aaron Mace

(57) ABSTRACT

A method, system, and computer program product for peer exchange of data between injection systems. A first injection system may store a plurality of injection control data sets, determine a first subset of the plurality of injection control data sets according to which the first injection system is configured to control delivery of fluid to a patient, provide the first subset of the plurality of injection control data sets for selection of an injection control data set for use in delivering fluid to the patient with the first injection system, and transmit the plurality of injection control data sets to at least one second injection system.

16 Claims, 7 Drawing Sheets

(58) Field of Classification Search
USPC .......................................................... 705/2
See application file for complete search history.

(56) References Cited

U.S. PATENT DOCUMENTS

| | | | |
|---|---|---|---|
| 6,581,117 | B1 | 6/2003 | Klein et al. |
| 6,602,488 | B1 | 8/2003 | Daghighian |
| 6,643,537 | B1 | 11/2003 | Zatezalo et al. |
| 7,094,216 | B2 | 8/2006 | Trombley, III et al. |
| 7,457,804 | B2 | 11/2008 | Uber et al. |
| 7,556,619 | B2 | 7/2009 | Spohn et al. |
| 7,933,782 | B2 | 4/2011 | Reiner et al. |
| 7,996,381 | B2 | 8/2011 | Uber, III et al. |
| 8,147,464 | B2 | 4/2012 | Spohn et al. |
| 8,198,599 | B2 | 6/2012 | Bouton et al. |
| 8,337,456 | B2 | 12/2012 | Schriver et al. |
| 8,521,716 | B2 | 8/2013 | Uber, III et al. |
| 8,540,698 | B2 | 9/2013 | Spohn et al. |
| 9,326,742 | B2 | 5/2016 | Hirschman et al. |
| 9,750,953 | B2 | 9/2017 | Kalafut |
| 2002/0165193 | A1 | 11/2002 | Greene et al. |
| 2003/0023155 | A1 | 1/2003 | Tsunoda |
| 2004/0082918 | A1 | 4/2004 | Evans et al. |
| 2004/0185049 | A1 | 9/2004 | Hunter et al. |
| 2004/0193453 | A1 | 9/2004 | Butterfield et al. |
| 2004/0205343 | A1 | 10/2004 | Forth et al. |
| 2005/0129170 | A1 | 6/2005 | Watson et al. |
| 2007/0019849 | A1 | 1/2007 | Kaufman et al. |
| 2007/0282965 | A1 | 12/2007 | Kataoka |
| 2008/0010384 | A1 | 1/2008 | Rechterman et al. |
| 2008/0071209 | A1* | 3/2008 | Moubayed ............ A61M 5/172 604/67 |
| 2008/0071210 | A1 | 3/2008 | Moubayed et al. |
| 2008/0086087 | A1 | 4/2008 | Spohn et al. |
| 2008/0109250 | A1 | 5/2008 | Walker et al. |
| 2008/0131362 | A1 | 6/2008 | Rousso et al. |
| 2008/0200870 | A1 | 8/2008 | Palmroos et al. |
| 2008/0212877 | A1 | 9/2008 | Franco |
| 2008/0294096 | A1 | 11/2008 | Uber, III et al. |
| 2009/0022377 | A1 | 1/2009 | Matsue et al. |
| 2009/0257949 | A1 | 10/2009 | Hefti et al. |
| 2009/0285469 | A1 | 11/2009 | Callahan et al. |
| 2010/0112011 | A1 | 5/2010 | Friedberg |
| 2010/0183206 | A1 | 7/2010 | Carlsen et al. |
| 2010/0183208 | A1 | 7/2010 | Kondo et al. |
| 2010/0185040 | A1 | 7/2010 | Uber, III et al. |
| 2011/0057634 | A1 | 3/2011 | Kunimatsu et al. |
| 2011/0076317 | A1 | 3/2011 | Alessi et al. |
| 2011/0093504 | A1 | 4/2011 | Butler et al. |
| 2011/0119212 | A1 | 5/2011 | De et al. |
| 2011/0191822 | A1 | 8/2011 | Pinsky et al. |
| 2011/0209764 | A1 | 9/2011 | Uber et al. |
| 2012/0110651 | A1* | 5/2012 | Van Biljon ............ G06Q 30/04 726/4 |
| 2012/0123257 | A1 | 5/2012 | Stokes, Jr. et al. |
| 2012/0219615 | A1 | 8/2012 | Hershberg et al. |
| 2012/0233215 | A1 | 9/2012 | Walker |
| 2012/0283691 | A1 | 11/2012 | Barnes et al. |
| 2013/0123567 | A1 | 5/2013 | Agamaite et al. |
| 2013/0259891 | A1 | 10/2013 | Harn, Jr. et al. |
| 2014/0039446 | A1 | 2/2014 | Day |
| 2015/0057634 | A1 | 2/2015 | Mastrototaro et al. |
| 2015/0370973 | A1 | 12/2015 | Jones |
| 2017/0116373 | A1 | 4/2017 | Ginsburg et al. |
| 2017/0258986 | A1* | 9/2017 | Tsoukalis ............... G16H 20/17 |
| 2018/0147347 | A1* | 5/2018 | Drost ................. A61M 5/1452 |
| 2019/0287661 | A1 | 9/2019 | Nobre et al. |
| 2020/0030524 | A1 | 1/2020 | Nemoto et al. |
| 2020/0098461 | A1 | 3/2020 | Macoviak et al. |
| 2020/0150508 | A1 | 5/2020 | Patterson et al. |
| 2020/0237452 | A1 | 7/2020 | Wolf et al. |
| 2020/0268980 | A1 | 8/2020 | Haury et al. |
| 2020/0297922 | A1 | 9/2020 | Chassot et al. |

FOREIGN PATENT DOCUMENTS

| | | |
|---|---|---|
| RU | 2429467 C2 | 9/2011 |
| WO | 9945783 A1 | 9/1999 |
| WO | 0123004 A1 | 4/2001 |
| WO | 2008021661 A2 | 2/2008 |
| WO | 2008083313 A2 | 7/2008 |
| WO | 2009042577 A2 | 4/2009 |
| WO | 2011137374 A1 | 11/2011 |
| WO | 2012155035 A1 | 11/2012 |
| WO | 2016196098 A1 | 12/2016 |
| WO | WO-2016196098 A1 * | 12/2016 .............. A61M 5/14 |

OTHER PUBLICATIONS

International Search Report and Written Opinion from PCT Application No. PCT/ US2012/066792, dated Feb. 6, 2013, filed Nov. 28, 2012.
"International Search Report and Written Opinion from PCT Application No. PCT/US2018/040817", dated Dec. 17, 2018.
"Partial International Search Report from PCT Application No. PCT/US2018/040817", dated Oct. 26, 2018.
Anonymous., "Natural language processing—Wikipedia, the free encyclopedia retrieved from internet: URL: http://en.wikipedia.org/w/index.php?title=Natural_language_processing&oldid=460032699 [retrieved on Apr. 28, 2015]", Nov. 10, 2011.
Bracco., "The Centralized, Server-Based System for Standardized Contrast Delivery Management—NEXO", Brochure, 2014.
CT Scan Protocols. Dr. Elliot K. Fishman. www.CTisus.com, Feb. 14, 2014.
"International Preliminary Report on Patentability from PCT Application No. PCT/US2018/040817", dated Jan. 16, 2020.
MEDRAD Stellant with Certegra Workstation Operation Manual, Catalog #SCT 310, 3033828 Rev. C, 2012, Indianola, PA, USA.
SIBUN.: 'Language Determination: Natural Language Processing from Scanned Document Images.', [Online] 1994, XP003031315 Retrieved from the Internet: <URL:http://citeseerx.ist.psu.edu/viewdoc/ summary?doi=10.1.1.14.8980> [retrieved on Jan. 18, 2013].

* cited by examiner

Administered 87.3 ml of 370 mg/ml ULTRAVIST using 18 gauge via right antecubital.

| | | | | | |
|---|---|---|---|---|---|
| Injection Start: | 20 November 2017 2:51 pm | | Patient Name: | Jane Doe | |
| Accession Number: | 725546571 | | Date of Birth: | 08 June 1976 | |
| Patient ID: | 19ECZ13N63UUK | | Weight: | 65 kg | |
| Image Created: | 20 November 2017 2:52 pm | | Height: | 164 cm | |

CARDIAC CTA

| Programmed | | ml/s | ml | Actual | | ml/s | ml |
|---|---|---|---|---|---|---|---|
| 1 | A | 5.00 | 75.0 | 1 | A | 4.80 | 75.4 |
| 2 | A 30% | 5.00 | 40.0 | 2 | A 30% | 4.94 | 39.6 |
| 3 | B | 5.00 | 30.0 | 3 | B | 4.75 | 30.0 |

| | | | | |
|---|---|---|---|---|
| Total Contrast(A): | 87.0 ml | | Total Contrast(A): | 87.3 ml |
| Total Saline(B): | 58.0 ml | | Total Saline(B): | 57.7 ml |
| Delay: | — | | | |
| Pressure Limit: | 325 psi | | | |

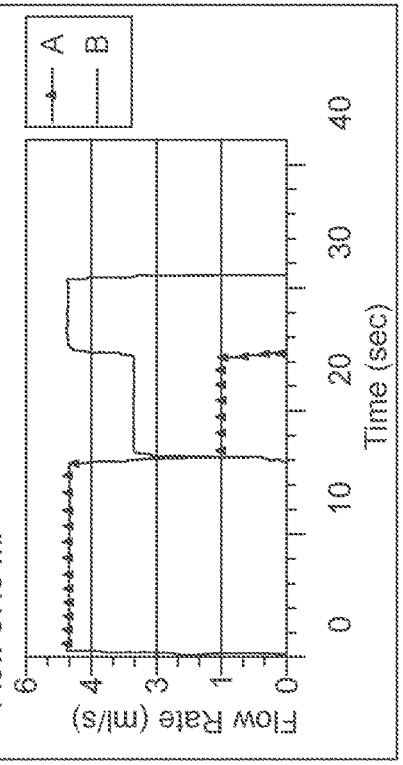

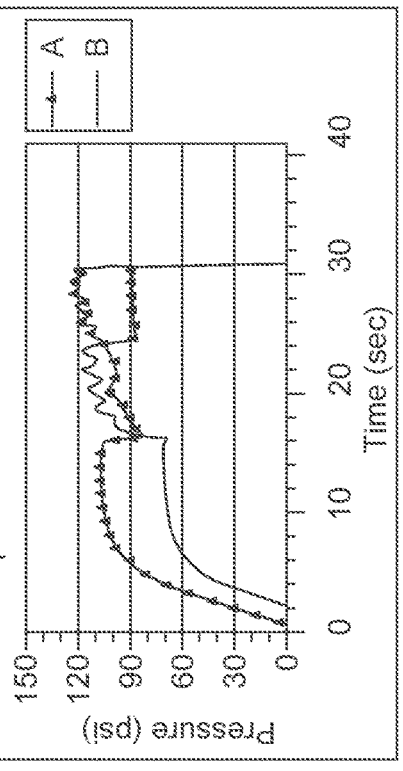

FIG. 7A

| Injection | Contrast | Saline | Fluid Usage | Contrast | Saline |
|---|---|---|---|---|---|
| Peak Pressure: | 112 psi | 125 psi | Loaded: | 130.1 ml | 150.9 ml |
| Peak Flow Rate: | 5.08 ml/s | 5.04 ml/s | Used: | 87.3 ml | 57.7 ml |
| Injection Completed: | YES | | Remaining: | 42.8 ml | 93.2 ml |
| Transient Events: | NO | | Total Fluid: | 145.0 ml | |
| | | | Contrast Dose: | 32.294 gI | |
| | | | Dosing Factor: | 0.497 gI/kg | |

Contrast
Brand: ULTRAVIST
Concentration: 370 mg/ml
Vial Volume: 150.00
Lot Number: DRXC0E
Expiration Date: 30 December 2018

Procedure
Tech ID: WV
Injection Site: Right Antecubital
Catheter Gauge: ga 18
Injector Name: Injector Notes
No history of allergy

FIG. 7B

SYSTEM, METHOD, AND COMPUTER PROGRAM PRODUCT FOR PEER EXCHANGE OF DATA BETWEEN INJECTION SYSTEMS

CROSS-REFERENCE TO RELATED APPLICATIONS

This application is a 371 national phase application of International Patent Application No. PCT/US2018/040817, filed Jul. 3, 2018, and claims the benefit of U.S. Provisional Patent Application Ser. No. 62/529,605, filed Jul. 7, 2017, the entire disclosure of which is hereby incorporated by reference in its entirety.

BACKGROUND OF THE INVENTION

1. Field of the Invention

This disclosure relates generally to systems, devices, products, apparatus, and methods that are used for fluid injections, and in one particular embodiment, to a system, product, and method for peer exchange of data between injection systems.

2. Technical Considerations

Data associated with injection systems (e.g., contrast injection systems, etc.) can be managed either locally on the injection system itself (e.g., only at the injection system) or with a central server external to the injection system that provides the data to the injection system. For example, a central server can deploy data to injection systems that are connected to the central server. As an example, many injection systems have local data management abilities, and data may be created, updated for new equipment, modified, and/or deleted at an injection system.

Data management may include ensuring that multiple injection systems each have a proper set of data for managing operations of an imaging site. For an imaging site that includes multiple injection systems, maintaining the proper set of data on each of the multiple different injection systems can involve considerable effort and may cause missteps, particularly in a case of upgrades of equipment or changes in types of contrast agents used at the imaging site. A central server based solution for managing data of the multiple injection systems may be attractive because the central server reduces the effort associated with locally updating each individual injection system and can add review and supervisory capabilities to the management process.

However, deploying and maintaining the central server adds an additional product that may require engagement with information technology (IT) departments and/or add significant adoption challenges. For example, larger imaging sites with larger numbers of injection systems may accept the burden of deploying a central server, but most imaging sites are smaller imaging sites with relatively smaller numbers of injection systems. Further, if the central server is unavailable; data may not be updated at an individual injection system, which may be operating or in use while the central server is unavailable. Moreover, data management at individual injection systems may be delayed due to processing resources and/or communication bandwidth being limited by the central server. In this way, an additional, separate, central server for managing data of multiple injection systems at an imaging site may not provide acceptable, efficient; secure; robust, and/or scalable data management.

Further, a cloud based central server model is simply an extension of the idea of a central server to serve multiple imaging sites from a single server. For example, a cloud based central server has similar challenges related to acceptance, efficiency, security, availability, and/or scalability. As an example, a cloud based central server requires individual injection systems to be connected to an external network that is not under the direct control of the imaging site.

SUMMARY OF THE INVENTION

Accordingly, provided are improved systems, devices, products, apparatus, and/or methods for peer exchange of data between injection systems.

According to a non-limiting embodiment or aspect, provided is a computer-implemented method for peer exchange of data between injection systems comprising: storing, with at least one first injection system, a plurality of injection control data sets; determining, with the at least one first injection system; a first subset of the plurality of injection control data sets according to which the at least one first injection system is configured to control delivery of at least one fluid to a patient; providing, at the at least one first injection system, the first subset of the plurality of injection control data sets for selection of an injection control data set for use in delivering the at least one fluid to the patient with the at least one first injection system; and transmitting, with the at least one first injection system, the plurality of injection control data sets to at least one second injection system.

In some non-limiting embodiments or aspects, the method further comprises: providing, with the at least one first injection system, the first subset of the plurality of injection control data sets to a user without providing a remainder of the plurality of injection control data sets to the user; receiving, with the at least one first injection system, user input; determining, with the at least one first injection system, a selected injection control data set for delivering the at least one fluid to the patient from the first subset of the plurality of injection control data sets based on the user input; and controlling, with the at least one first injection system, delivery of the at least one fluid to the patient according to the selected injection control data set.

In some non-limiting embodiments or aspects, the at least one first injection system is configured to control delivery of the at least one fluid to the patient based on the first subset of the plurality of injection control data sets, wherein the at least one second injection system is configured to control delivery of one or more fluids to the patient based on a second subset of the plurality of injection control data sets, and wherein the second subset includes at least one injection control data set different than the first subset.

In some non-limiting embodiments or aspects, the at least one first injection system is not configured to control delivery of the at least one fluid to the patient based on the at least one different injection control data set.

In some non-limiting embodiments or aspects, the method further comprises: determining, with the at least one second injection system, a second subset of the plurality of injection control data sets according to which the at least one second injection system is configured to control delivery of one or more fluids to the patient; and providing, with the at least one second injection system, the second subset of the plurality of injection control data sets for selection of an injection control data set for use in delivering the one or more fluids to the patient with the at least one second injection system.

In some non-limiting embodiments or aspects, the method further comprises: providing, with the at least one second injection system, the second subset of the plurality of injection control data sets to a user without providing a remainder of the plurality of injection control data sets to the user; receiving, with the at least one second injection system, user input; determining, with the at least one second injection system, a selected injection control data set for use in delivering the one or more fluids to the patient from the second subset of the plurality of injection control data sets based on the user input; and controlling, with the at least one second injection system, delivery of the one or more fluids to the patient according to the selected injection control data set.

In some non-limiting embodiments or aspects, the at least one first injection system includes a first type of injection system, wherein the at least one second injection system includes a second type of injection system, and wherein the first type of injection system is different than the second type of injection system.

In some non-limiting embodiments or aspects, the method further comprises: storing, with the at least one first injection system, a plurality of identifiers associated with a plurality of injection systems including the at least one first injection system; the at least one second injection system, and at least one third injection system; and modifying, with the at least one first injection system, one or more injection control data sets of the plurality of injection protocols, wherein the one or more injection control data sets are associated with at least one identifier of the at least one third injection system; and transmitting, with the at least one first injection system, the plurality of identifiers to the at least one second injection system.

In some non-limiting embodiments or aspects, the plurality of injection control data sets include a plurality of injection protocols, the method further comprising: receiving, with the at least one first injection system, a selection of an injection protocol from the first subset or use in delivering the at least one fluid to the patient with the at least one first injection system; and delivering, with the at least one first injection system, the at least one fluid to the patient according to the selected injection protocol.

In some non-limiting embodiments or aspects, the plurality of injection control data sets include a plurality of presets; the method further comprising: receiving, with the at least one first injection system, a selection of a preset from the first subset for use in delivering the at least one fluid to the patient with the at least one first injection system; receiving, with the at least one first injection system, patient data associated with the patient and procedure data associated with a procedure to be performed on the patient; determining, with the at least one first injection system, an injection protocol for use in delivering the at least one fluid to the patient with the at least one first injection system based on the selected preset, the patient data, and the procedure data; and delivering, with the at least one first injection system, the at least one fluid to the patient according to the determined injection protocol.

In some non-limiting embodiments or aspects, the method further comprises: receiving, with the at least one first injection system, at least one of (i) accessory data associated with a plurality of catheters and (ii) fluid data associated with a plurality of fluids; receiving, with the at least one first injection system, a selection of the injection control data set from the first subset for use in delivering the at least one fluid to the patient with the at least one injector system; determining, with the at least one first injection system, at least one of (i) a subset of the plurality of catheters for use in delivering the at least one fluid to the patient and (ii) a subset of the plurality of fluids for use in delivering the at least one fluid to the patient, based on the selected injection control data set; and providing, with the at least one first injection system, the at least one of (i) the subset of the plurality of catheters, for selection of a catheter for using in delivering the at least one fluid to the patient, and (ii) the subset of the plurality of fluids, for selection of a fluid for use in delivering the at least one fluid to the patient.

According to a non-limiting embodiment or aspects, provided is a peer exchange data management system comprising: at least one first injection system configured to control delivery of at least one fluid to a patient, wherein the at least one first injection system includes at least one processor programmed or configured to: store a plurality of injection control data sets; determine a first subset of the plurality of injection control data sets according to which the at least one first injection system is configured to control delivery of the at least one fluid to the patient; provide the first subset of the plurality of injection control data sets for selection of an injection control data set for use in delivering the at least one fluid to the patient with the at least one first injection system; and transmit the plurality of injection control data sets to at least one second injection system.

In some non-limiting embodiments or aspects, the at least one first injection system is further programmed or configured to: provide the first subset of the plurality of injection control data sets to a user without providing a remainder of the plurality of injection control data sets to the user; receive user input; determine a selected injection control data set for delivering the at least one fluid to the patient from the first subset of the plurality of injection control data sets based on the user input; and control delivery of the at least one fluid to the patient according to the selected injection control data set.

In some non-limiting embodiments or aspects, the at least one first injection system is configured to control delivery of the at least one fluid to the patient based on the first subset of the plurality of injection control data sets, wherein the at least one second injection system is configured to control delivery of one or more fluids to the patient based on a second subset of the plurality of injection control data sets, and wherein the second subset includes at least one injection control data set different than the first subset.

In some non-limiting embodiments or aspects, the at least one first injection system is not configured to control delivery of the at least one fluid to the patient based on the at least one different injection control data set.

In some non-limiting embodiments or aspects, the system further comprises: the at least one second injection system configured to deliver one or more fluids to the patient, wherein the at least one second injection system includes at least one processor programmed or configured to: determine a second subset of the plurality of injection control data sets according to which the at least one second injection system is configured to control delivery of the one or more fluids to the patient; and provide the second subset of the plurality of injection control data sets for selection of an injection control data set for use in delivering the one or more fluids to the patient with the at least one second injection system.

In some non-limiting embodiments or aspects, the at least one second injection system is further programmed or configured to: provide the second subset of the plurality of injection control data sets to a user without providing a remainder of the plurality of injection control data sets to the user; receive user input; determine a selected injection control data set for use in delivering the one or more fluids to the patient from the second subset of the plurality of injection control data sets based on the user input; and control delivery of the one or more fluids to the patient according to the selected injection control data set.

In some non-limiting embodiments or aspects, the at least one first injection system includes a first type of injection system, wherein the at least one second injection system includes a second type of injection system, and wherein the first type of injection system is different than the second type of injection system.

In some non-limiting embodiments or aspects; the at least one first injection system is further programmed or configured to: store a plurality of identifiers associated with a plurality of injection systems including the at least one first injection system, the at least one second injection system, and at least one third injection system; and modify one or more injection control data sets of the plurality of injection protocols, wherein the one or more injection control data sets are associated with at least one identifier of the at least one third injection system; and transmit the plurality of identifiers to the at least one second injection system.

In some non-limiting embodiments or aspects, the plurality of injection control data sets include a plurality of injection protocols, and wherein the at least one first injection system is further programmed or configured to: receive a selection of an injection protocol from the first subset or use in delivering the at least one fluid to the patient with the at least one first injection system; and deliver the at least one fluid to the patient according to the selected injection protocol.

In some non-limiting embodiments or aspects, the plurality of injection control data sets include a plurality of presets, and wherein the at least one first injection system is further programmed or configured to: receive a selection of a preset from the first subset or use in delivering the at least one fluid to the patient with the at least one first injection system; receive patient data associated with the patient and procedure data associated with a procedure to be performed on the patient; determine an injection protocol for use in delivering the at least one fluid to the patient with the at least one first injection system based on the selected preset, the patient data, and the procedure data; and deliver the at least one fluid to the patient according to the determined injection protocol.

In some non-limiting embodiments or aspects, the at least one first injection system is further programmed or configured to: receive at least one of (i) accessory data associated with a plurality of catheters and (ii) fluid data associated with a plurality of fluids; receive a selection of the injection control data set from the first subset or use in delivering the at least one fluid to the patient with the at least one injector system; determine at least one of (i) a subset of the plurality of catheters for use in delivering the at least one fluid to the patient and (ii) a subset of the plurality of fluids for use in delivering the at least one fluid to the patient, based on the selected injection control data set; and provide the at least one of (i) the subset of the plurality of catheters, for selection of a catheter for using in delivering the at least one fluid to the patient, and (ii) the subset of the plurality of fluids, for selection of a fluid for use in delivering the at least one fluid to the patient.

According to a non-limiting embodiment or aspect, provided is a computer program product for peer exchange of data between injection systems, the computer program product comprising at least one non-transitory computer-readable medium comprising one or more instructions that, when executed by at least one processor, cause the at least one processor to: store a plurality of injection control data sets in at least one first injection system; determine a first subset of the plurality of injection control data sets according to which the at least one first injection system is configured to control delivery of the at least one fluid to the patient; provide, at the at least one first injection system, the first subset of the plurality of injection control data sets for selection of an injection control data set for use in delivering the at least one fluid to the patient with the at least one first injection system; and transmit the plurality of injection control data sets from the at least one first injection system to at least one second injection system.

According to a non-limiting embodiment or aspect, provided is a computer-implemented method for peer exchange of data between injection systems comprising: determining, with an injection system in a peer-to-peer network including a plurality of injection systems, a query for prior exam data associated with a patient; transmitting, with the injection system, the query to at least one other injection system in the peer-to-peer network including the plurality of injection systems; receiving, with the injection system, a response to the query from the at least one other injection system in the peer-to-peer network, wherein the response to the query includes the prior exam data, and wherein the prior exam data includes at least one record associated with at least one prior exam performed on the patient; and providing, with the injection system, the prior exam data via a user interface.

In some non-limiting embodiments or aspects, the method further comprises: determining, with the injection system, an injection control data set for use in delivering at least one fluid to the patient with the injection system based on the at least one record.

In some non-limiting embodiments or aspects, the at least one record comprises a plurality of records, wherein the plurality of records include a plurality of injection control data sets according to which the at least one fluid was injected into the patient during a plurality of prior exams, the method further comprising: receiving, with the injection system via the user interface, a selection, from the plurality of injection control data sets, of the injection control data set for use in delivering the at least one fluid to the patient with the injection system; and controlling, with the injection system, delivery of the at least one fluid to the patient according to the selected injection control data set.

In some non-limiting embodiments or aspects, the method further comprises: receiving, with the injection system via the user interface, user input; modifying, with the injection system, the injection control data set based on the user input; and controlling, with the injection system, delivery of the at least one fluid to the patient according to the modified injection control data set.

In some non-limiting embodiments or aspects, the at least one record includes at least one of the following: (a) patient data associated with the patient, (b) an injection control data set according to which at least one fluid was injected into the patient during the at least one prior exam, (c) injection system settings data associated with the at least one other injection system at which the at least one prior exam was performed, (d) accessory data associated with a type of catheter through which the at least one fluid was injected into the patient during the at least one prior exam, (e) procedure data associated with an injection site on the patient at which the catheter was located during the at least one prior exam, or any combination thereof.

In some non-limiting embodiments or aspects, the patient data includes at least one of the following parameters associated with the patient: (i) a first name of the patient, (ii) a last name of the patient, (iii) a weight of the patient, (iv) a height of the patient, (v) a gender of the patient, (vi) a date of birth of the patient, (vii) a unique identifier of the patient, or any combination thereof.

In some non-limiting embodiments or aspects, the injection control data set includes an injection protocol including at least one of the following parameters according to which the at least one fluid is injected into the patient during the at least one prior exam: (i) a volume of a first fluid of the at least one fluid programmed to be injected into the patient, (ii) a volume of a second fluid of the at least one fluid programmed to be injected into the patient, (iii) a volume of the first fluid of the at least one fluid injected into the patient during the at least one prior exam, (iv) a volume of the second fluid of the at least one fluid injected into the patient during the at least one prior exam, (v) a flow rate at which the first fluid of the at least one fluid was programmed to be injected into the patient, (vi) a flow rate at which the second fluid of the at least one fluid was programmed to be injected into the patient, (vii) a flow rate at which the first fluid of the at least one fluid was injected into the patient during the at least one prior exam, (viii) a flow rate at which the second fluid of the at least one fluid was injected into the patient during the at least one prior exam, (ix) a pressure threshold defining a maximum pressure generated via the at least one fluid within the at least one other injection system during the at least one prior exam, (x) a start time for the at least one prior exam, and (xi) an end time for the at least one prior exam, or any combination thereof.

In some non-limiting embodiments or aspects; the injection system settings data includes at least one of the following parameters associated with a configuration of the at least one other injection system at which the at least one prior exam is performed: (i) a unit of weight measure used by the injection system, (ii) a unit of pressure used by the injection system, (iii) a language used by the injection system; (iv) a date selected as a reminder to calibrate the injection system, (v) a volume selected for audio provided by the injection system, (vi) a current date and/or time used by the injection system, (vii) a format for the date used by the injection system, (viii) a format for the time used by the injection system, (ix) a setting indicative of an availability of injector-scanner interfacing (ISI), or any combination thereof.

According to a non-limiting embodiment or aspect, provided is a peer exchange data management system comprising: an injection system in a peer-to-peer network including a plurality of injection systems, wherein the injection system is configured to control delivery of at least one fluid to a patient, and wherein the injection system includes at least one processor programmed or configured to: determine a query for prior exam data associated with the patient; transmit the query to at least one other injection system in the peer-to-peer network including the plurality of injection systems; receive a response to the query from the at least one other injection system in the peer-to-peer network, wherein the response to the query includes the prior exam data, and wherein the prior exam data includes at least one record associated with at least one prior exam performed on the patient; and provide the prior exam data via a user interface.

In some non-limiting embodiments or aspects, the injection system is further programmed or configured to: determine an injection control data set for use in delivering the at least one fluid to the patient with the injection system based on the at least one record.

In some non-limiting embodiments or aspects, the at least one record comprises a plurality of records, wherein the plurality of records include a plurality of injection control data sets according to which the at least one fluid was injected into the patient during a plurality of prior exams, and wherein the injection system is further programmed or configured to: receive, via the user interface, a selection, from the plurality of injection control data sets; of the injection control data set for use in delivering the at least one fluid to the patient with the injection system; and control delivery of the at least one fluid to the patient according to the selected injection control data set.

In some non-limiting embodiments or aspects, the injection system is further programmed or configured to: receive via the user interface, user input; modify the injection control data set based on the user input; and control delivery of the at least one fluid to the patient according to the modified injection control data set.

In some non-limiting embodiments or aspects, the at least one record includes at least one of the following: (a) patient data associated with the patient, (b) an injection control data set according to which at least one fluid was injected into the patient during the at least one prior exam, (c) injection system settings data associated with the at least one other injection system at which the at least one prior exam was performed, (d) accessory data associated with a type of catheter through which the at least one fluid was injected into the patient during the at least one prior exam, (e) procedure data associated with an injection site on the patient at which the catheter was located during the at least one prior exam, or any combination thereof.

In some non-limiting embodiments or aspects, the patient data includes at least one of the following parameters associated with the patient: (i) a first name of the patient, (ii) a last name of the patient, (iii) a weight of the patient, (iv) a height of the patient, (v) a gender of the patient, (vi) a date of birth of the patient, (vii) a unique identifier of the patient, or any combination thereof.

In some non-limiting embodiments or aspects, the injection control data set includes an injection protocol including at least one of the following parameters according to which the at least one fluid is injected into the patient during the at least one prior exam: (i) a volume of a first fluid of the at least one fluid programmed to be injected into the patient, (ii) a volume of a second fluid of the at least one fluid programmed to be injected into the patient, (iii) a volume of the first fluid of the at least one fluid injected into the patient during the at least one prior exam, (iv) a volume of the second fluid of the at least one fluid injected into the patient during the at least one prior exam, (v) a flow rate at which the first fluid of the at least one fluid was programmed to be injected into the patient, (vi) a flow rate at which the second fluid of the at least one fluid was programmed to be injected into the patient, (vii) a flow rate at which the first fluid of the at least one fluid was injected into the patient during the at least one prior exam, (viii) a flow rate at which the second fluid of the at least one fluid was injected into the patient during the at least one prior exam; (ix) a pressure threshold defining a maximum pressure generated via the at least one fluid within the at least one other injection system during the at least one prior exam, (x) a start time for the at least one prior exam, and (xi) an end time for the prior exam, or any combination thereof.

In some non-limiting embodiments or aspects, the injection system settings data includes at least one of the following parameters associated with a configuration of the at least one other injection system at which the at least one prior exam is performed: (i) a unit of weight measure used by the injection system, (ii) a unit of pressure used by the injection system, (iii) a language used by the injection system; (iv) a date selected as a reminder to calibrate the injection system, (v) a volume selected for audio provided by the injection system, (vi) a current date and/or time used by the injection system, (vii) a format for the date used by the injection system, (viii) a format for the time used by the injection system, (ix) a setting indicative of an availability of injector-scanner interfacing (ISI), or any combination thereof.

According to a non-limiting embodiment or aspect, provided is a computer program product for peer exchange of data between injection systems, the computer program product comprising at least one non-transitory computer-readable medium comprising one or more instructions that, when executed by at least one processor, cause the at least one processor to: determine, at an injection system in a peer-to-peer network including a plurality of injection systems; a query for prior exam data associated with a patient; transmit the query to at least one other injection system in the peer-to-peer network including the plurality of injection systems; receive a response to the query from the at least one other injection system in the peer-to-peer network, wherein the response to the query includes the prior exam data, and wherein the prior exam data includes at least one record associated with at least one prior exam performed on the patient; and provide the prior exam data via a user interface.

According to a non-limiting embodiment or aspect, provided is a computer-implemented method for peer exchange of data between injection systems comprising: storing, with an injection system in a peer-to-peer network including a plurality of injection systems configured to control delivery fluid to a patient, data associated with the plurality of injection systems; modifying, with the injection system, the data; automatically transmitting; with the injection system, in response to modifying the data, the modified data to at least one other injection system in the peer-to-peer network including the plurality of injection systems.

According to a non-limiting embodiment or aspect, provided is a peer exchange data management system comprising: an injection system in a peer-to-peer network including a plurality of injection systems, wherein the injection system is configured to control delivery of fluid to a patient, and wherein the injection system includes at least one processor programmed or configured to: store data associated with the plurality of injection systems; modify the data; automatically transmit, in response to modifying the data, the modified data to at least one other injection system in the peer-to-peer network including the plurality of injection systems.

According to a non-limiting embodiment or aspect, provided is a computer program product for peer exchange of data between injection systems, the computer program product comprising at least one non-transitory computer-readable medium comprising one or more instructions that, when executed by at least one processor, cause the at least one processor to: store, at an injection system in a peer-to-peer network including a plurality of injection systems configured to control delivery of fluid to a patient, data associated with the plurality of injection systems; modify the data; and automatically transmit, in response to modifying the data, the modified data to at least one other injection system in the peer-to-peer network including the plurality of injection systems.

Further non-limiting embodiments or aspects are set forth in the following numbered clauses:

Clause 1. A computer-implemented method for peer exchange of data between injection systems comprising: storing, with at least one first injection system; a plurality of injection control data sets; determining; with the at least one first injection system, a first subset of the plurality of injection control data sets according to which the at least one first injection system is configured to control delivery of at least one fluid to a patient; providing, at the at least one first injection system, the first subset of the plurality of injection control data sets for selection of an injection control data set for use in delivering the at least one fluid to the patient with the at least one first injection system; and transmitting, with the at least one first injection system, the plurality of injection control data sets to at least one second injection system.

Clause 2. The computer-implemented method of clause 1, further comprising: providing; with the at least one first injection system, the first subset of the plurality of injection control data sets to a user without providing a remainder of the plurality of injection control data sets to the user; receiving, with the at least one first injection system, user input; determining, with the at least one first injection system; a selected injection control data set for delivering the at least one fluid to the patient from the first subset of the plurality of injection control data sets based on the user input; and controlling; with the at least one first injection system, delivery of the at least one fluid to the patient according to the selected injection control data set.

Clause 3. The computer-implemented method of any of clauses 1 and 2, wherein the at least one first injection system is configured to control delivery of the at least one fluid to the patient based on the first subset of the plurality of injection control data sets, wherein the at least one second injection system is configured to control delivery of one or more fluids to the patient based on a second subset of the plurality of injection control data sets, and wherein the second subset includes at least one injection control data set different than the first subset.

Clause 4. The computer-implemented method of any of clauses 1-3, wherein the at least one first injection system is not configured to control delivery of the at least one fluid to the patient based on the at least one different injection control data set.

Clause 5. The computer-implemented method of any of clauses 1-4, further comprising: determining, with the at least one second injection system, a second subset of the plurality of injection control data sets according to which the at least one second injection system is configured to control delivery of one or more fluids to the patient; and providing; with the at least one second injection system; the second subset of the plurality of injection control data sets for selection of an injection control data set for use in delivering the one or more fluids to the patient with the at least one second injection system.

Clause 6. The computer-implemented method of any of clauses 1-5, further comprising: providing; with the at least one second injection system, the second subset of the plurality of injection control data sets to a user without providing a remainder of the plurality of injection control data sets to the user; receiving, with the at least one second injection system, user input; determining, with the at least one second injection system, a selected injection control data set for use in delivering the one or more fluids to the patient from the second subset of the plurality of injection control data sets based on the user input: and controlling, with the at least one second injection system, delivery of the one or more fluids to the patient according to the selected injection control data set.

Clause 7. The computer-implemented method of any of clauses 1-6, wherein the at least one first injection system includes a first type of injection system, wherein the at least one second injection system includes a second type of injection system, and wherein the first type of injection system is different than the second type of injection system.

Clause 8. The computer-implemented method of any of clauses 1-7, further comprising: storing, with the at least one first injection system, a plurality of identifiers associated with a plurality of injection systems including the at least one first injection system, the at least one second injection system, and at least one third injection system; and modifying, with the at least one first injection system, one or more injection control data sets of the plurality of injection protocols, wherein the one or more injection control data sets are associated with at least one identifier of the at least one third injection system; and transmitting, with the at least one first injection system, the plurality of identifiers to the at least one second injection system.

Clause 9. The computer-implemented method of any of clauses 1-8, wherein the plurality of injection control data sets include a plurality of injection protocols, the method further comprising: receiving, with the at least one first injection system, a selection of an injection protocol from the first subset or use in delivering the at least one fluid to the patient with the at least one first injection system; and delivering, with the at least one first injection system, the at least one fluid to the patient according to the selected injection protocol.

Clause 10. The computer-implemented method of any of clauses 1-9, wherein the plurality of injection control data sets include a plurality of presets, the method further comprising: receiving, with the at least one first injection system, a selection of a preset from the first subset for use in delivering the at least one fluid to the patient with the at least one first injection system: receiving, with the at least one first injection system, patient data associated with the patient and procedure data associated with a procedure to be performed on the patient; determining, with the at least one first injection system, an injection protocol for use in delivering the at least one fluid to the patient with the at least one first injection system based on the selected preset, the patient data, and the procedure data; and delivering, with the at least one first injection system, the at least one fluid to the patient according to the determined injection protocol.

Clause 11. The computer-implemented method of any of clauses 1-10, further comprising: receiving, with the at least one first injection system, at least one of (i) accessory data associated with a plurality of catheters and (ii) fluid data associated with a plurality of fluids; receiving, with the at least one first injection system, a selection of the injection control data set from the first subset for use in delivering the at least one fluid to the patient with the at least one injector system; determining, with the at least one first injection system, at least one of (i) a subset of the plurality of catheters for use in delivering the at least one fluid to the patient and (ii) a subset of the plurality of fluids for use in delivering the at least one fluid to the patient, based on the selected injection control data set; and providing, with the at least one first injection system, the at least one of (i) the subset of the plurality of catheters, for selection of a catheter for using in delivering the at least one fluid to the patient, and (ii) the subset of the plurality of fluids, for selection of a fluid for use in delivering the at least one fluid to the patient.

Clause 12. A peer exchange data management system comprising: at least one first injection system configured to control delivery of at least one fluid to a patient, wherein the at least one first injection system includes at least one processor programmed or configured to: store a plurality of injection control data sets; determine a first subset of the plurality of injection control data sets according to which the at least one first injection system is configured to control delivery of the at least one fluid to the patient; provide the first subset of the plurality of injection control data sets for selection of an injection control data set for use in delivering the at least one fluid to the patient with the at least one first injection system; and transmit the plurality of injection control data sets to at least one second injection system.

Clause 13. The system of clause 12, wherein the at least one first injection system is further programmed or configured to: provide the first subset of the plurality of injection control data sets to a user without providing a remainder of the plurality of injection control data sets to the user; receive user input; determine a selected injection control data set for delivering the at least one fluid to the patient from the first subset of the plurality of injection control data sets based on the user input; and control delivery of the at least one fluid to the patient according to the selected injection control data set.

Clause 14. The system of any of clauses 12 and 13, wherein the at least one first injection system is configured to control delivery of the at least one fluid to the patient based on the first subset of the plurality of injection control data sets, wherein the at least one second injection system is configured to control delivery of one or more fluids to the patient based on a second subset of the plurality of injection control data sets, and wherein the second subset includes at least one injection control data set different than the first subset.

Clause 15. The system of any of clauses 12-14, wherein the at least one first injection system is not configured to control delivery of the at least one fluid to the patient based on the at least one different injection control data set.

Clause 16. The system of any of clauses 12-15, further comprising: the at least one second injection system configured to deliver one or more fluids to the patient, wherein the at least one second injection system includes at least one processor programmed or configured to: determine a second subset of the plurality of injection control data sets according to which the at least one second injection system is configured to control delivery of the one or more fluids to the patient; and provide the second subset of the plurality of injection control data sets for selection of an injection control data set for use in delivering the one or more fluids to the patient with the at least one second injection system.

Clause 17. The system of any of clauses 12-16, wherein the at least one second injection system is further programmed or configured to: provide the second subset of the plurality of injection control data sets to a user without providing a remainder of the plurality of injection control data sets to the user; receive user input; determine a selected injection control data set for use in delivering the one or more fluids to the patient from the second subset of the plurality of injection control data sets based on the user input; and control delivery of the one or more fluids to the patient according to the selected injection control data set.

Clause 18. The system of any of clauses 12-17, wherein the at least one first injection system includes a first type of injection system, wherein the at least one second injection system includes a second type of injection system, and wherein the first type of injection system is different than the second type of injection system.

Clause 19. The system of any of clauses 12-18, wherein the at least one first injection system is further programmed or configured to: store a plurality of identifiers associated with a plurality of injection systems including the at least one first injection system, the at least one second injection system, and at least one third injection system; and modify one or more injection control data sets of the plurality of injection protocols; wherein the one or more injection control data sets are associated with at least one identifier of the at least one third injection system; and transmit the plurality of identifiers to the at least one second injection system.

Clause 20. The system of any of clauses 12-19, wherein the plurality of injection control data sets include a plurality of injection protocols, and wherein the at least one first injection system is further programmed or configured to: receive a selection of an injection protocol from the first subset or use in delivering the at least one fluid to the patient with the at least one first injection system; and deliver the at least one fluid to the patient according to the selected injection protocol.

Clause 21. The system of any of clauses 12-20, wherein the plurality of injection control data sets include a plurality of presets, and wherein the at least one first injection system is further programmed or configured to: receive a selection of a preset from the first subset or use in delivering the at least one fluid to the patient with the at least one first injection system; receive patient data associated with the patient and procedure data associated with a procedure to be performed on the patient; determine an injection protocol for use in delivering the at least one fluid to the patient with the at least one first injection system based on the selected preset, the patient data, and the procedure data; and deliver the at least one fluid to the patient according to the determined injection protocol.

Clause 22. The system of any of clauses 12-21, wherein the at least one first injection system is further programmed or configured to: receive at least one of (i) accessory data associated with a plurality of catheters and (ii) fluid data associated with a plurality of fluids; receive a selection of the injection control data set from the first subset or use in delivering the at least one fluid to the patient with the at least one injector system; determine at least one of (i) a subset of the plurality of catheters for use in delivering the at least one fluid to the patient and (ii) a subset of the plurality of fluids for use in delivering the at least one fluid to the patient, based on the selected injection control data set; and provide the at least one of (i) the subset of the plurality of catheters, for selection of a catheter for using in delivering the at least one fluid to the patient, and (ii) the subset of the plurality of fluids, for selection of a fluid for use in delivering the at least one fluid to the patient.

Clause 23. A computer program product for peer exchange of data between injection systems, the computer program product comprising at least one non-transitory computer-readable medium comprising one or more instructions that, when executed by at least one processor, cause the at least one processor to: store a plurality of injection control data sets in at least one first injection system; determine a first subset of the plurality of injection control data sets according to which the at least one first injection system is configured to control delivery of the at least one fluid to the patient; provide, at the at least one first injection system, the first subset of the plurality of injection control data sets for selection of an injection control data set for use in delivering the at least one fluid to the patient with the at least one first injection system; and transmit the plurality of injection control data sets from the at least one first injection system to at least one second injection system.

Clause 24. A computer-implemented method for peer exchange of data between injection systems comprising: determining, with an injection system in a peer-to-peer network including a plurality of injection systems, a query for prior exam data associated with a patient; transmitting, with the injection system, the query to at least one other injection system in the peer-to-peer network including the plurality of injection systems; receiving, with the injection system, a response to the query from the at least one other injection system in the peer-to-peer network, wherein the response to the query includes the prior exam data, and wherein the prior exam data includes at least one record associated with at least one prior exam performed on the patient; and providing, with the injection system, the prior exam data via a user interface.

Clause 25. The computer-implemented method of clause 24, further comprising: determining, with the injection system, an injection control data set for use in delivering at least one fluid to the patient with the injection system based on the at least one record.

Clause 26. The computer-implemented method of any of clauses 24 and 25, wherein the at least one record comprises a plurality of records, wherein the plurality of records include a plurality of injection control data sets according to which the at least one fluid was injected into the patient during a plurality of prior exams, the method further comprising: receiving, with the injection system via the user interface, a selection, from the plurality of injection control data sets, of the injection control data set for use in delivering the at least one fluid to the patient with the injection system; and controlling, with the injection system, delivery of the at least one fluid to the patient according to the selected injection control data set.

Clause 27. The computer-implemented method of any of clauses 24-26, further comprising: receiving, with the injection system via the user interface, user input; modifying, with the injection system, the injection control data set based on the user input; and controlling, with the injection system, delivery of the at least one fluid to the patient according to the modified injection control data set.

Clause 28. The computer-implemented method of any of clauses 24-27, wherein the at least one record includes at least one of the following: (a) patient data associated with the patient, (b) an injection control data set according to which at least one fluid was injected into the patient during the at least one prior exam, (c) injection system settings data associated with the at least one other injection system at which the at least one prior exam was performed, (d) accessory data associated with a type of catheter through which the at least one fluid was injected into the patient during the at least one prior exam, (e) procedure data associated with an injection site on the patient at which the catheter was located during the at least one prior exam, or any combination thereof.

Clause 29. The computer-implemented method of any of clauses 24-28, wherein the patient data includes at least one of the following parameters associated with the patient: (i) a first name of the patient, (ii) a last name of the patient, (iii) a weight of the patient, (iv) a height of the patient, (v) a gender of the patient, (vi) a date of birth of the patient, (vii) a unique identifier of the patient, or any combination thereof.

Clause 30. The computer-implemented method of any of clauses 24-29, wherein the injection control data set includes an injection protocol including at least one of the following parameters according to which the at least one fluid is injected into the patient during the at least one prior exam: (i) a volume of a first fluid of the at least one fluid programmed to be injected into the patient, (ii) a volume of a second fluid of the at least one fluid programmed to be injected into the patient, (iii) a volume of the first fluid of the at least one fluid injected into the patient during the at least one prior exam, (iv) a volume of the second fluid of the at least one fluid injected into the patient during the at least one prior exam, (v) a flow rate at which the first fluid of the at least one fluid was programmed to be injected into the patient, (vi) a flow rate at which the second fluid of the at least one fluid was programmed to be injected into the patient, (vii) a flow rate at which the first fluid of the at least one fluid was injected into the patient during the at least one prior exam, (viii) a flow rate at which the second fluid of the at least one fluid was injected into the patient during the at least one prior exam, (ix) a pressure threshold defining a maximum pressure generated via the at least one fluid within the at least one other injection system during the at least one prior exam, (x) a start time for the at least one prior exam, and (xi) an end time for the at least one prior exam, or any combination thereof.

Clause 31. The computer-implemented method of any of clauses 24-30, wherein the injection system settings data includes at least one of the following parameters associated with a configuration of the at least one other injection system at which the at least one prior exam is performed: (i) a unit of weight measure used by the injection system, (ii) a unit of pressure used by the injection system, (iii) a language used by the injection system; (iv) a date selected as a reminder to calibrate the injection system, (v) a volume selected for audio provided by the injection system, (vi) a current date and/or time used by the injection system, (vii) a format for the date used by the injection system, (viii) a format for the time used by the injection system, (ix) a setting indicative of an availability of injector-scanner interfacing (ISI), or any combination thereof.

Clause 32. A peer exchange data management system comprising: an injection system in a peer-to-peer network including a plurality of injection systems, wherein the injection system is configured to control delivery of at least one fluid to a patient, and wherein the injection system includes at least one processor programmed or configured to: determine a query for prior exam data associated with the patient; transmit the query to at least one other injection system in the peer-to-peer network including the plurality of injection systems; receive a response to the query from the at least one other injection system in the peer-to-peer network, wherein the response to the query includes the prior exam data, and wherein the prior exam data includes at least one record associated with at least one prior exam performed on the patient; and provide the prior exam data via a user interface.

Clause 33. The system of clause 32, wherein the injection system is further programmed or configured to: determine an injection control data set for use in delivering the at least one fluid to the patient with the injection system based on the at least one record.

Clause 34, The system of any of clauses 32 and 33, wherein the at least one record comprises a plurality of records, wherein the plurality of records include a plurality of injection control data sets according to which the at least one fluid was injected into the patient during a plurality of prior exams, and wherein the injection system is further programmed or configured to: receive, via the user interface, a selection, from the plurality of injection control data sets, of the injection control data set for use in delivering the at least one fluid to the patient with the injection system; and control delivery of the at least one fluid to the patient according to the selected injection control data set.

Clause 35. The system of any of clauses 32-34, wherein the injection system is further programmed or configured to: receive via the user interface, user input; modify the injection control data set based on the user input; and control delivery of the at least one fluid to the patient according to the modified injection control data set.

Clause 36, The system of any of clauses 32-35, wherein the at least one record includes at least one of the following: (a) patient data associated with the patient, (b) an injection control data set according to which at least one fluid was injected into the patient during the at least one prior exam, (c) injection system settings data associated with the at least one other injection system at which the at least one prior exam was performed, (d) accessory data associated with a type of catheter through which the at least one fluid was injected into the patient during the at least one prior exam, (e) procedure data associated with an injection site on the patient at which the catheter was located during the at least one prior exam, or any combination thereof.

Clause 37. The system of any of clauses 32-36, wherein the patient data includes at least one of the following parameters associated with the patient: (i) a first name of the patient, (ii) a last name of the patient, (iii) a weight of the patient, (iv) a height of the patient, (v) a gender of the patient, (vi) a date of birth of the patient, (vii) a unique identifier of the patient, or any combination thereof.

Clause 38. The system of any of clauses 32-37, wherein the injection control data set includes an injection protocol including at least one of the following parameters according to which the at least one fluid is injected into the patient during the at least one prior exam: (i) a volume of a first fluid of the at least one fluid programmed to be injected into the patient, (ii) a volume of a second fluid of the at least one fluid programmed to be injected into the patient, (iii) a volume of the first fluid of the at least one fluid injected into the patient during the at least one prior exam, (iv) a volume of the second fluid of the at least one fluid injected into the patient during the at least one prior exam, (v) a flow rate at which the first fluid of the at least one fluid was programmed to be injected into the patient, (vi) a flow rate at which the second fluid of the at least one fluid was programmed to be injected into the patient, (vii) a flow rate at which the first fluid of the at least one fluid was injected into the patient during the at least one prior exam, (viii) a flow rate at which the second fluid of the at least one fluid was injected into the patient during the at least one prior exam, (ix) a pressure threshold defining a maximum pressure generated via the at least one fluid within the at least one other injection system during the at least one prior exam, (x) a start time for the at least one prior exam, and (xi) an end time for the prior exam, or any combination thereof.

Clause 39, The system of any of clauses 32-38, wherein the injection system settings data includes at least one of the following parameters associated with a configuration of the at least one other injection system at which the at least one prior exam is performed: (i) a unit of weight measure used by the injection system, (ii) a unit of pressure used by the injection system, (iii) a language used by the injection system; (iv) a date selected as a reminder to calibrate the injection system, (v) a volume selected for audio provided by the injection system, (vi) a current date and/or time used by the injection system, (vii) a format for the date used by the injection system, (viii) a format for the time used by the injection system, (ix) a setting indicative of an availability of injector-scanner interfacing (ISI), or any combination thereof.

Clause 40. A computer program product for peer exchange of data between injection systems, the computer program product comprising at least one non-transitory computer-readable medium comprising one or more instructions that, when executed by at least one processor, cause the at least one processor to: determine, at an injection system in a peer-to-peer network including a plurality of injection systems, a query for prior exam data associated with a patient; transmit the query to at least one other injection system in the peer-to-peer network including the plurality of injection systems; receive a response to the query from the at least one other injection system in the peer-to-peer network, wherein the response to the query includes the prior exam data, and wherein the prior exam data includes at least one record associated with at least one prior exam performed on the patient; and provide the prior exam data via a user interface.

Clause 41. A computer-implemented method for peer exchange of data between injection systems comprising: storing, with an injection system in a peer-to-peer network including a plurality of injection systems configured to control delivery fluid to a patient, data associated with the plurality of injection systems; modifying, with the injection system, the data; automatically transmitting, with the injection system, in response to modifying the data, the modified data to at least one other injection system in the peer-to-peer network including the plurality of injection systems.

Clause 42. A peer exchange data management system comprising: an injection system in a peer-to-peer network including a plurality of injection systems, wherein the injection system is configured to control delivery of fluid to a patient, and wherein the injection system includes at least one processor programmed or configured to: store data associated with the plurality of injection systems; modify the data; automatically transmit, in response to modifying the data, the modified data to at least one other injection system in the peer-to-peer network including the plurality of injection systems.

Clause 43. A computer program product for peer exchange of data between injection systems, the computer program product comprising at least one non-transitory computer-readable medium comprising one or more instructions that, when executed by at least one processor, cause the at least one processor to: store, at an injection system in a peer-to-peer network including a plurality of injection systems configured to control delivery of fluid to a patient, data associated with the plurality of injection systems; modify the data; and automatically transmit, in response to modifying the data, the modified data to at least one other injection system in the peer-to-peer network including the plurality of injection systems.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a," "an," and "the" include plural referents unless the context clearly dictates otherwise.

BRIEF DESCRIPTION OF THE DRAWINGS

Additional advantages and details of the invention are explained in greater detail below with reference to the exemplary embodiments or aspects that are illustrated in the accompanying schematic figures, in which:

FIGS. 7A-7B show an implementation of a display of data and/or information of a non-limiting embodiment or aspect of one or more systems or one or more devices of FIGS. 1A-1E.

DETAILED DESCRIPTION OF THE INVENTION

Figure 1A:
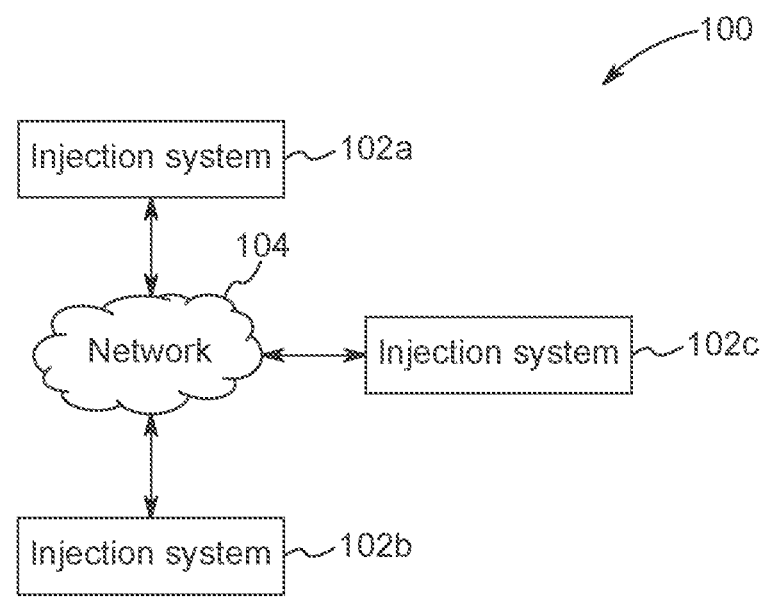
FIG. 1A is a diagram of a non-limiting embodiment or aspect of an environment in which systems, devices, products, apparatus, and/or methods, described herein, may be implemented according to the principles of the present invention.

For purposes of the description hereinafter, the terms "end," "upper," "lower," "right," "left," "vertical," "horizontal," "top," "bottom," "lateral," "longitudinal," and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments or aspects of the invention. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one."

Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible. It will be appreciated that numerous other arrangements are possible.

As used herein, the term "server" may refer to one or more computing devices, such as processors, storage devices, and/or similar computer components that communicate with client devices and/or other computing devices over a network, such as the Internet or private networks, and, in some examples, facilitate communication among other servers and/or client devices. It will be appreciated that various other arrangements are possible. As used herein, the term "system" may refer to one or more computing devices or combinations of computing devices such as, but not limited to, processors, servers, client devices, software applications, and/or other like components. In addition, reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

Non-limiting embodiments or aspects of the present invention are directed to systems, methods and computer program products for peer exchange of data (e.g., injection control data, patient data, injection system settings data, fluid data, accessory data, preset data, prior exam data, etc.) between injection systems. In some non-limiting embodiments or aspects, a method may include storing, with at least one first injection system, a plurality of injection protocols; determining, with the at least one first injection system, a first subset of the plurality of injection protocols according to which the at least one first injection system is configured to deliver fluid to a patient; providing, with the at least one first injection system, the first subset of the plurality of injection protocols for delivering fluid to the patient with the at least one first injection system; and transmitting, with the at least one first injection system, the plurality of injection protocols to at least one second injection system. In some non-limiting embodiments or aspects, a method may include determining, with an injection system in a peer-to-peer network including a plurality of injection systems, a query for prior exam data associated with a patient; transmitting, with the injection system, the query to at least one other injection system in the peer-to-peer network including the plurality of injection systems; receiving, with the injection system, a response to the query from the at least one other injection system in the peer-to-peer network, wherein the response to the query includes the prior exam data, and wherein the prior exam data includes at least one record associated with at least one prior exam performed on the patient; and providing, with the injection system, the prior exam data via a user interface. In some non-limiting embodiments or aspects, a method may include storing, with an injection system in a peer-to-peer network including a plurality of injection systems configured to control delivery of at least one fluid to a patient, data associated with the plurality of injection systems; modifying, with the injection system, the data; automatically transmitting, with the injection system, in response to modifying the data, the modified data to at least one other injection system in the peer-to-peer network including the plurality of injection systems.

In this way, embodiments or aspects of the present invention may provide a decentralized approach to data management (e.g., explicit membership of injection systems in a peer-to-peer network, etc.) that enables more acceptable, efficient, secure, robust, and/or scalable data management between injection systems. For example, such a decentralized approach may provide local and/or remote sharing of data between injection systems (e.g., between injection systems at a same location; between injection systems at different remote locations, between injection systems of different imaging sites, etc.). As an example, a full backup of all injection control data sets (e.g., all injection protocols, all presets, etc.) for all injection systems in the peer-to-peer network can be maintained at and/or provided from an individual injection system (e.g., at each injection system in the peer-to-peer network of injection systems, etc.), and the individual injection system can maintain its own subset of injection protocols for use with that individual injection system. Accordingly, data management at injection systems can be more easily adopted or implemented (e.g., without adding an additional server and associated maintenance thereof, etc.), data can be received or updated at an individual injection system anytime a peer connection to one or more peer injection systems is available, a larger number of resources for processing and/or communicating data between injection systems can be accessed, data can be exchanged in a more secure manner, and/or a number of injection systems at an imaging site can be more easily increased.

Referring now to FIG. 1A, FIG. 1A is a diagram of an example environment 100 in which devices, systems, and/or methods, described herein, may be implemented. As shown in FIG. 1A, environment 100 includes a plurality of injection systems 102 (e.g., first injection system 102*a*, second injection system 102*b*, third injection system 102*c*, etc.) and network 104. The plurality of injection systems 102 may interconnect (e.g., establish a connection to communicate) via wired connections, wireless connections, or a combination of wired and wireless connections.

Figure 1B:
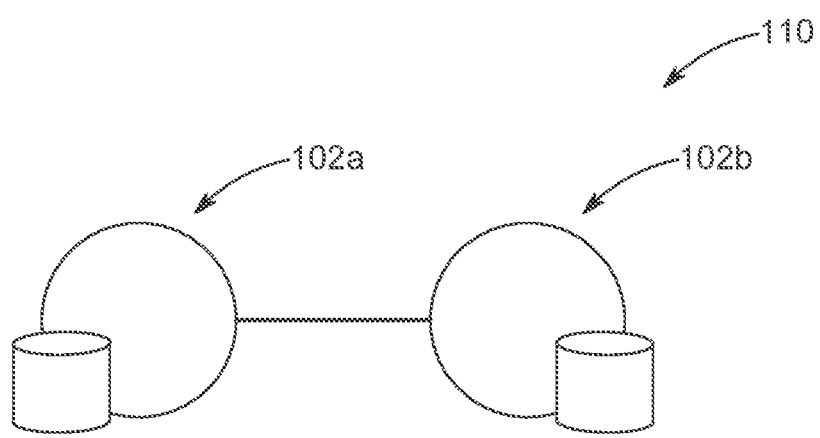
FIG. 1B is a diagram of logical connections or a virtual overlay network for an implementation of a non-limiting embodiment or aspect of a peer-to-peer network of systems or devices of FIG. 1A.
Figure 1C:
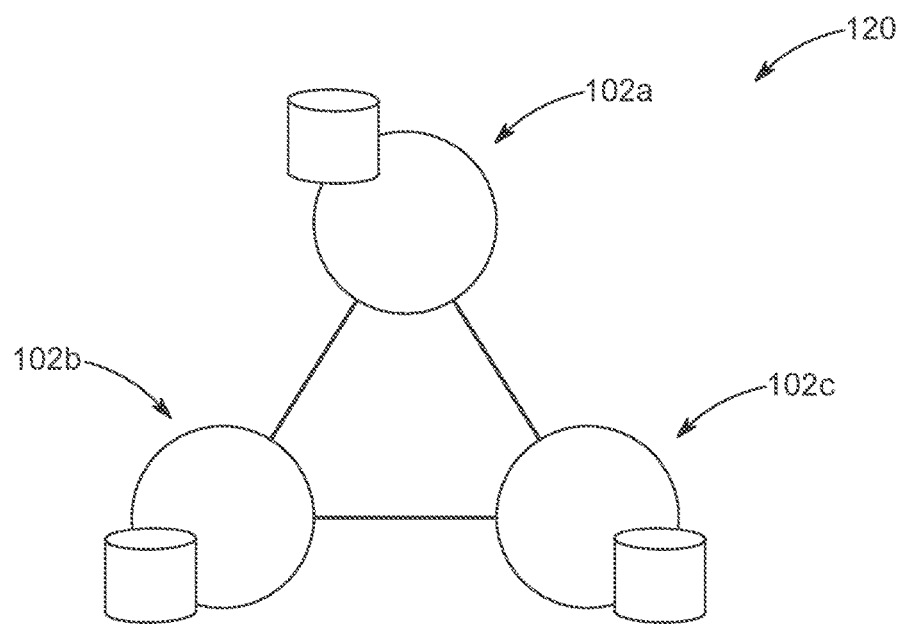
FIG. 1C is a diagram of logical connections or a virtual overlay network for an implementation of a non-limiting embodiment or aspect of a peer-to-peer network of systems or devices of FIG. 1A.

Referring also to FIGS. 1B-1E, in some non-limiting embodiments or aspects, the plurality of injection systems 102 include a peer-to-peer network of injection systems. For example, a peer-to-peer network formed by the plurality of injection systems 102 may implement logical connections or a virtual overlay network between injection systems (e.g., peer nodes, etc.) on top of a physical network topology (e.g., on top of network 104, etc.), where the injection systems or peer nodes in the logical connections or virtual overlay network form a subset of the nodes in the physical network (e.g., a subset of nodes in network 104). As an example, FIG. 1B shows logical connections or a virtual overlay network for an implementation of a non-limiting embodiment or aspect of a peer-to-peer network 110 of the plurality of injection systems 102 including two injection systems or peer nodes 102a and 102b. As an example, FIG. 1C shows logical connections or a virtual overlay network for an implementation of a non-limiting embodiment or aspect of a peer-to-peer network 120 of the plurality of injection systems 102 including three injection systems or peer nodes 102a, 102b and 102c. In such examples, data may be communicated over the underlying physical network (e.g., over network 104, over an underlying TCP/IP network, etc.); however, injection systems or peer nodes (e.g., nodes at an application layer) are able to communicate with each other directly, via the logical connections or virtual overlay links, which correspond to paths through the underlying physical network.

Figure 1D:
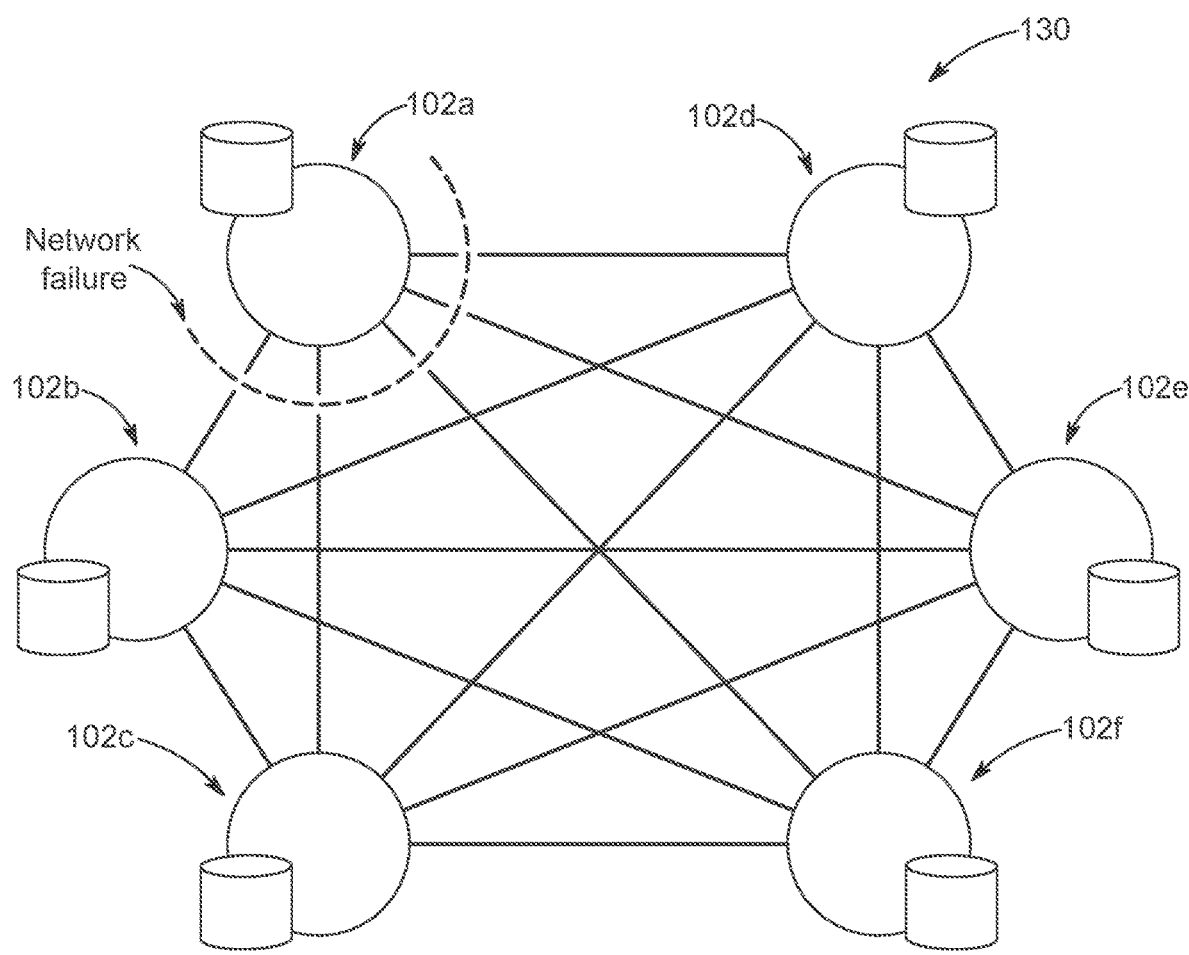
FIG. 1D is a diagram of logical connections or a virtual overlay network for an implementation of a non-limiting embodiment or aspect of a peer-to-peer network of systems or devices of FIG. 1A.

FIG. 1D is a diagram of logical connections or a virtual overlay network for an implementation of a non-limiting embodiment or aspect of a peer-to-peer network 130 of the plurality of injection systems 102 including six injection systems or peer nodes 102a, 102b, 102c, 102d, 102e, and 102f. In some non-limiting embodiments or aspects, a number of logical connections or direct virtual overlay links L between nodes in a peer-to-peer network may be determined according to the following Equation (1):

$$L = (N*(N-1)/2) \quad (1)$$

where N is a number of injection systems or peer nodes in the peer-to-peer network. For example, as shown in FIG. 1D, there may be fifteen logical connections or direct virtual overlay links L between the six injection systems or peer nodes 102a, 102b, 102c, 102d, 102e, and 102f of peer-to-peer network 130. As also shown in FIG. 1D, in some non-limiting embodiments or aspects, one or more injection systems or peer nodes of a peer-to-peer network (e.g., injection system or peer node 102a in peer-to-peer network 130) may be partitioned by a network failure from one or more other injection systems or peer nodes of the peer-to-peer network (e.g., injection systems or peer nodes 102b, 102c, 102d, 102e, and 102f of peer-to-peer network 130); however, communications can be maintained between injection systems or peer nodes in the peer-to-peer network that are not partitioned by the network failure (e.g., between injection systems or peer nodes 102b, 102c, 102d, 102e, and 102f of peer-to-peer network 130).

Figure 1E:
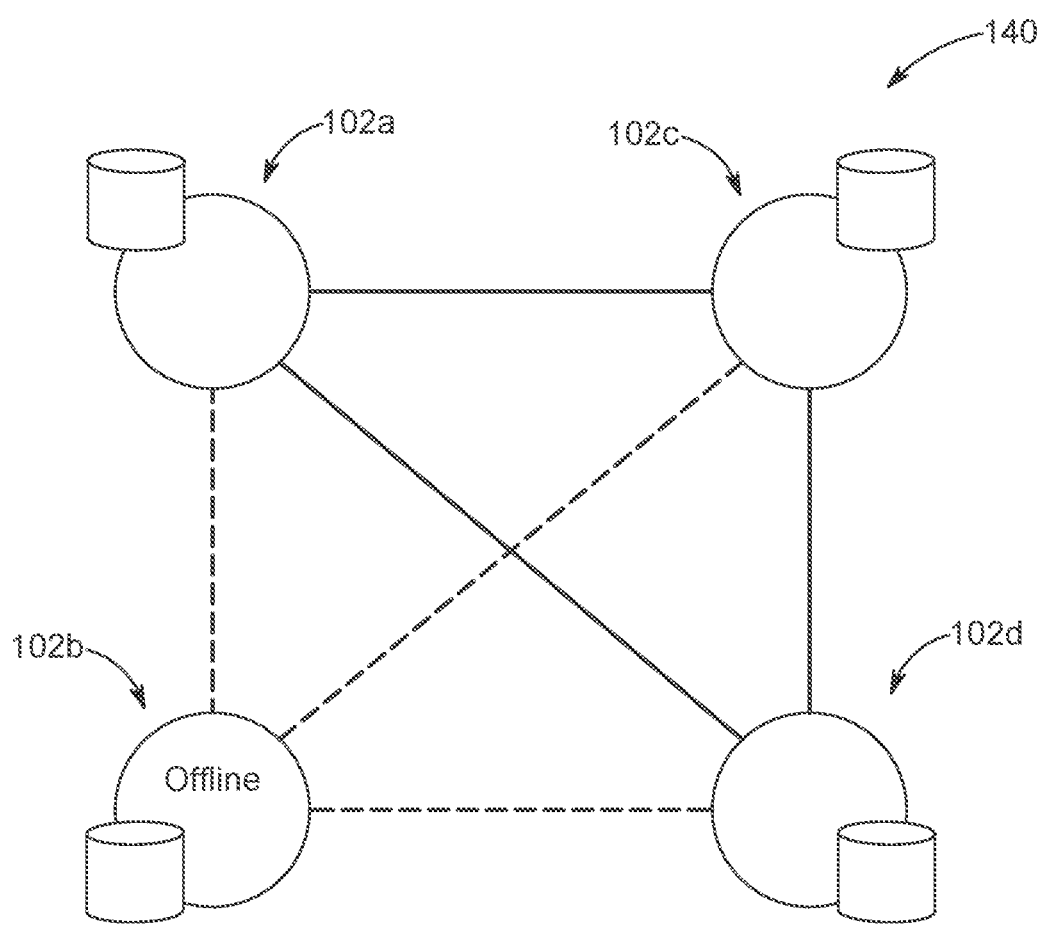
FIG. 1E is a diagram of logical connections or a virtual overlay network for an implementation of a non-limiting embodiment or aspect of a peer-to-peer network of systems or devices of FIG. 1A.

FIG. 1E is a diagram of logical connections or a virtual overlay network for an implementation of a non-limiting embodiment or aspect of a peer-to-peer network 140 of the plurality of injection systems 102 including four injection systems or peer nodes 102a, 102b, 102c, and 102d. As shown in FIG. 1E, there may be six logical connections or direct virtual overlay links L between the four injection systems or peer nodes 102a, 102b, 102c, and 102d. As also shown in FIG. 1D, in some non-limiting embodiments or aspects, one or more injection systems or peer nodes of a peer-to-peer network (e.g., injection system or peer node 102b in peer-to-peer network 140) may be offline and/or not communicating with other systems or nodes; however, communications can be maintained between injection systems or peer nodes in the peer-to-peer network which are online and/or communicating with other systems or nodes (e.g., between injection systems or peer nodes 102a, 102c, and 102d of peer-to-peer network 140).

In some non-limiting embodiments or aspects, one or more injection systems of the plurality of injection systems 102 include one or more devices capable of receiving data and/or information (e.g., injection control data, patient data, injection system settings data, fluid data, accessory data, preset data, prior exam data, etc.) from and/or communicating data and/or information (e.g., injection control data, patient data, injection system settings data, fluid data, accessory data, preset data, prior exam data, etc.) to each other (e.g., via a peer-to-peer network of the plurality of injection systems 102 as peer nodes on top of a physical network including network 104, etc.). For example, one or more injection systems of the plurality of injection systems 102 can include a computing device, such as a one or more computers, portable computers (e.g., tablet computers), mobile devices (e.g., cellular phones, smartphones, wearable devices, such as watches, glasses, lenses, and/or clothing, PDAs, and/or the like), a server (e.g., a transaction processing server), a group of servers, and/or other like devices. In some non-limiting embodiments or aspects, one or more injection systems of the plurality of injection systems 102 are in communication with a data storage device, which may be local or remote to the one or more injection systems of the plurality of injection systems 102. In some non-limiting embodiments or aspects, one or more injection systems of the plurality of injection systems 102 are capable of receiving data and/or information from, storing data and/or information in, communicating data and/or information to, or searching data and/or information stored in the data storage device (e.g., injection control data, patient data, injection system settings data, fluid data, accessory data, preset data, prior exam data, etc.).

In some non-limiting embodiments or aspects, injection control data includes one or more injection control data sets according to which one or more injection systems of the plurality of injection systems 102 is configured to control delivery of fluid to a patient. For example, an injection control data set may include an injection protocol according to which one or more injection systems of the plurality of injection systems 102 is configured to control delivery of fluid to a patient, a preset according to which one or more injection systems of the plurality of injection systems 102 is configured to control delivery of fluid to a patient, and/or the like.

In some non-limiting embodiments or aspects, an injection protocol includes at least one of the following parameters according to which at least one fluid is injected into a patient during an exam, procedure, or injection: (i) a volume of a first fluid of the at least one fluid programmed to be injected into the patient, (ii) a volume of a second fluid of the at least one fluid programmed to be injected into the patient, (iii) a volume of the first fluid of the at least one fluid injected into the patient during the exam, (iv) a volume of the second fluid of the at least one fluid injected into the patient during the exam, (v) a flow rate at which the first fluid of the at least one fluid is programmed to be injected into the patient, (vi) a flow rate at which the second fluid of the at least one fluid is programmed to be injected into the patient, (vii) a flow rate at which the first fluid of the at least one fluid is injected into the patient during the exam, (viii) a flow rate at which the second fluid of the at least one fluid is injected into the patient during the exam, (ix) a pressure threshold defining a maximum pressure allowed to be generated via the at least one fluid within an injection system during the exam, (x) a start time for the prior exam, and (xi) an end time for the prior exam, or any combination thereof. For example, an injection protocol can include a protocol for the delivery of a fluid volume over time where the fluid volume includes at least a volumetric amount of a first fluid (e.g., Fluid A), such as contrast agent, delivered at a flow rate that may vary over time and may be zero at certain times, and a volumetric amount of a second fluid (e.g., Fluid B), such as saline, which also may be delivered at a flow rate that may vary over time and may be zero at certain times. As an example, an injection protocol can include parameters (e.g., total volume, flow rate over time, etc.) for delivering the contrast agent with an injection system. In such an example, parameters of an injection protocol can be defined to achieve a desired bolus profile or shape. In some examples, a protocol can include parameters for a multi-phase injection of contrast agent and/or saline into a patient, for example, a first (e.g., a contrast only) phase, a second (e.g., an admixture) phase in which contrast and/or saline are injected at a desired ratio, and third (e.g., a flush) phase with saline).

In some non-limiting embodiments or aspects, a preset includes one or more parameters (e.g., input parameters, preset parameters, etc.) that can be used to generate one or more injection protocols for a patient when combined with patient data of the patient and/or procedure data of a procedure to be performed on the patient (e.g., a type of procedure to be performed, fluid data associated with one or more fluids to be used, accessory data associated with one or more accessories to be used, a location of an injection site on a body of the patient, etc.). As an example; a user and/or the injection system can input (e.g., preset, specify before a time for a fluid injection and/or before patient data and/or procedure data is known, etc.) values for the one or more parameters as a preset to be used to generate an injection protocol, and at the time for the fluid injection select the preset and input the patient data for a specific patient (e.g., patient weight, patient height, etc.) and/or the procedure data for a specific procedure to be performed on the patient (e.g., contrast concentration, injection site on the patient, etc.), in response to which the injection system generates the injection protocol for the specific patient and procedure based on the selected preset. In such an example, the parameters may include one or more of the following parameters: a contrast type, whether to include a test injection in the injection protocol, a fluid type for the test injection, a delivery method (e.g., by volume, duration, etc.) by which the test injection is calculated and delivered, a volume of the test injection, a duration of the test injection, whether to include a transit bolus in the injection protocol, a volume of a contrast bolus portion in the transit bolus, a volume of a saline bolus portion in the transit bolus, a maximum flow rate of the injection protocol, a duration adjustment (e.g., duration adjustment is used to calculate the duration for the first phase of the diagnostic protocol; the duration adjustment is added to the scan duration to determine the injection duration of the first phase of the injection protocol), a minimum injection duration of a contrast phase of the injection protocol, a saline flush volume of a saline flush phase of the injection protocol, a minimum time between when a phase containing contrast ends and when a scan ends, a maximum contrast volume of the injection protocol, a maximum saline volume of the injection protocol; a pressure limit, a scan duration (e.g., an amount of time for a diagnostic portion of a scan acquisition), a pressure limit, an amount of time for a diagnostic portion of a scan acquisition, a time at which peak enhancement is achieved during a transit bolus, a peak enhancement range during a transit bolus, an update to the scan duration based on the peak enhancement time and/or range, or any combination thereof. For example, preset data may include Personalized Patient Protocol (P3T®) presets and parameters of the MEDRAD® Stellant CT Injection System with Certegra® Workstation provided by Bayer, which can be used to generate an injection protocol (e.g., a P3T® injection protocol) based on preset data; patient data; and/or procedure data.

In some non-limiting embodiments or aspects, patient data includes one or more parameters associated with one or more patients, such as a first name of a patient, a last name of the patient, a weight of the patient, a height of the patient; a gender of the patient, a date of birth of the patient; a unique patient identifier of the patient (e.g., a social security number, a medical record number, etc.), one or more lab values of the patient, one or more allergies of the patient, and/or the like.

In some non-limiting embodiments or aspects; injection system settings data includes one or more parameters associated with one or more configurations or settings of one or more injection systems, such as a unit of weight measure (e.g., lb., kg., etc.) used by an injection system; a unit of pressure (e.g., psi, kPA, etc.) used by the injection system; a language (e.g., English, German, etc.) used by the injection system; a date selected as a reminder to calibrate the injection system; (v) a volume (e.g., loud, medium, soft, off, etc.) selected for audio output provided by the injection system; a current date/time used by the injection system; a format for the date (e.g.; MM/DD/YYYY, DD/MM/YYYY, etc.) used by the injection system; a format for the time (e.g., EST, GMT, 24 hour, 12 hour, etc.) used by the injection system; a setting (e.g., on or off) indicative of an availability of an injector-scanner interfacing (ISI); and/or the like.

In some non-limiting embodiments or aspects, fluid data includes one or more parameters of one or more fluids available at one or more injection systems, such as a name; brand, and/or type of the one or more fluids available at an injection system; a concentration of the one or more fluids available at the injection system, an amount of the one or more fluids available at the injection system, a presentation type (e.g., a vial size) of the one or more fluids at the injection system, and/or the like.

In some non-limiting embodiments or aspects; accessory data includes one or more parameters of one or more accessory devices available at one or more injection systems, such a type of the one or more accessory devices (e.g.; a syringe and/or a type thereof, patient/administration tubing and/or a type thereof; a T-connector and/or a type thereof, a catheter and/or a type thereof, a spike and/or a type thereof (e.g., for contrast and saline bags and bottles), a Quick-Fill tube and/or a type thereof, a multi-patient disposable set and/or a type thereof, and a single patient disposable set and/or a type thereof, an extravasation detector and/or a type thereof, etc.) available at an injection system; a number of the one or more accessory devices available at the injection system, and/or the like.

In some non-limiting embodiments or aspects, prior exam data includes data and/or information (e.g.; injection control data, patient data, injection system settings data, fluid data, accessory data, preset data, prior exam data, etc.) associated with one or more exams, procedures, and/or injections performed on one or more patients. For example, prior exam data may include at least one record associated with at least one prior exam performed on a patient (e.g., a record for each prior exam performed on the patient, etc.). As an example, at least one record associated with a patient may include at least one of the following: the following: (a) patient data associated with the patient, (b) an injection control data set according to which at least one fluid is injected into the patient during at least one prior exam, (c) injection system settings data associated with an injection system at which the at least one prior exam is performed, (d) accessory data associated with a type of catheter through which the at least one fluid is injected into the patient during the at least one prior exam, (e) procedure data associated with an injection site on the patient at which the catheter is located during the at least one prior exam, or any combination thereof. In such an example, prior exam data may include one or more parameters of the following parameters associated with a prior exam, such as a first name of the patient, a middle name of the patient, a last name of the patient, a date of birth of the patient, a gender of the patient, a height (e.g., cm, etc.) of the patient, a weight (e.g., kg, etc.) of the patient, an accession number of the exam, procedure, and/or injection, a study type identifier of the exam, procedure, and/or injection, a unique study identifier of the exam, procedure, and/or injection, a date of the exam, procedure, and/or injection, a description of the exam, procedure, and/or injection, a match status of the exam, procedure, and/or injection, an archive status of the exam, procedure, and/or injection, archived AEs, a unique identifier of a technologist for the exam, procedure, and/or injection, a catheter gauge used for the exam, procedure, and/or injection, user notes on the exam, procedure, and/or injection, a brand of a first fluid, a concentration of the first fluid, a lot number of the first fluid, a vial volume of the first fluid, an expiration date of the first fluid, a brand of a second fluid, a concentration of the second fluid, a lot number of the second fluid, a vial volume of the second fluid, an expiration date of the second fluid, a facility (e.g., an imaging site, etc.), a suite or room number, a scanner name, an injector name, an injector serial number, a serial number of the Certegra® Workstation or other informatics workstation used for the exam, an amount (e.g., ml, etc.) of the first fluid loaded, an amount of the first fluid delivered, an amount of the first fluid wasted, a peak flow rate (e.g., ml/s, etc.) of the first fluid, a peak pressure (e.g., psi, etc.) of the first fluid, a kind of the first fluid, a type of the first fluid, a new syringe used indicator (e.g., Y/N, etc.) for the first fluid, a type of syringe used for the first fluid, a cumulative syringe dock count for the first fluid, an amount (e.g., ml, etc.) of the second fluid loaded, an amount of the second fluid delivered, an amount of the second fluid wasted, a peak flow (e.g., ml/s, etc.) of the second fluid, a pressure (e.g., psi, etc.) of the second fluid, a kind of the second fluid, a type of the second fluid, a new syringe used indicator (e.g., YIN, etc.) for the second fluid, a type of syringe used for the second fluid, a cumulative syringe dock count for the second fluid, a protocol name, a protocol type, a start time, a stop time, a termination time, a transient event count, a description of the transient events, an exchange status, and/or the like.

In some non-limiting embodiments or aspects, one or more injection systems of the plurality of injection systems 102 include an application (e.g., a software application, etc.) associated with the plurality of injection systems 102, such as an application stored on first injection system 102a, an application stored on second injection system 102b, an application stored on third injection system 102c, a mobile application (e.g., a mobile device application, a native application for a mobile device, a mobile cloud application for a mobile device, and/or the like) stored on first injection system 102a, a mobile application stored on second injection system 102b, a mobile application stored on third injection system 102c, and/or the like. For example, the application may include a background service that hosts a web application based graphical user interface (GUI) that enables protocol management including communication of the data and/or information described herein between injection systems of the plurality of injection systems 102 without a central server. As an example, applications on the plurality of injection systems 102 may be configured with unique identifiers and/or internet protocol (IP) addresses of each other to form a peer-to-peer network (e.g., a mesh network, etc.) among the plurality of injection systems 102. In some non-limiting embodiments or aspects, a version of an application on an injection system of the plurality of injection systems 102 defers to an older and/or different version of the same application running on another injection system of the plurality of injection systems 102 (e.g., by forwarding users via an HTTP redirect, etc.) to ensure compatibility between the applications (e.g., data communication compatibility, data processing compatibility, etc.).

In some non-limiting embodiments or aspects, one or more injection systems of the plurality of injection systems 102 are configured to inject, deliver, or administer contrast fluid including a contrast agent to a patient, and in some non-limiting embodiments or aspects, one or more of the plurality of injection systems 102 are further configured to inject or administer saline or other fluid to a patient before, during, or after administration of contrast fluid. For example, one or more injection systems of the plurality of injection systems 102 can inject one or more prescribed dosages of contrast fluid directly into a patient's blood stream via a hypodermic needle and syringe. In some non-limiting embodiments or aspects, one or more injection systems of the plurality of injection systems 102 are configured to continually administer saline to a patient through a peripheral IV line (Ply) and catheter and one or more prescribed dosages of contrast fluid may be introduced into the PIV and administered via the catheter to the patient. In some non-limiting embodiments or aspects, one or more injection systems of the plurality of injection systems 102 are configured to inject a dose of contrast fluid followed by administration of a particular volume of saline.

In some non-limiting embodiments or aspects, one or more injection systems of the plurality of injection systems 102 are configured to administer a single contrast agent. In some non-limiting embodiments or aspects, one or more injection systems of the plurality of injection systems 102 are configured to deliver two or more different contrast agents. In implementations in which an injection system of the plurality of injection systems 102 is configured to deliver multiple contrast agents, the injection system may allow the operator to switch configurations depending on the intended procedure. An amount of each contrast agent delivered by the injection system may vary based on an injection protocol being used. For example, specific injection protocols can be used to achieve desired blood, plasma, and/or tissue levels of contrast agent. A physician or other qualified medical personnel (and/or the injection system or injection system) can determine an appropriate injection protocol according to which a contrast agent is to be delivered to a particular patient using metrics regarding the patient (e.g., age, weight, height, body mass index (BMI), cardiac output, a type of procedure to be performed, etc.), The one or more injection systems of the plurality of injection systems 102 may be configured to inject two or more contrast agents either individually, sequentially, or simultaneously. As such, in some non-limiting embodiments or aspects, one or more injection systems of the plurality of injection systems 102 include two or more reservoirs, such as vials or syringes capable of holding a radiopharmaceutical prior to administration. The one or more injection systems of the plurality of injection systems 102 may further include additional medical fluid reservoirs capable of holding, for example, saline, other drugs, or other fluids.

Exemplary injection systems or injectors are those that are disclosed in: U.S. patent application Ser. No. 09/715,330, filed on Nov. 17, 2000, issued as U.S. Pat. No. 6,643,537; U.S. patent application Ser. No. 09/982,518, filed on Oct. 18, 2001, issued as U.S. Pat. No. 7,094,216; U.S. patent application Ser. No. 10/825,866, filed on Apr. 16, 2004, issued as U.S. Pat. No. 7,556,619; U.S. patent application Ser. No. 12/437,011, filed May 7, 2009, issued as U.S. Pat. No. 8,337,456; U.S. patent application Ser. No. 12/476,513, filed Jun. 2, 2009, issued as U.S. Pat. No. 8,147,464; and U.S. patent application Ser. No. 11/004,670, filed on Dec. 3, 2004, issued as U.S. Pat. No. 8,540,698, the disclosures of each of which are incorporated herein by reference in their entireties. In some non-limiting embodiments or aspects, one or more injectors of the plurality of injectors include the MEDRAD® Stellant CT Injection System with Certegra® Workstation provided by Bayer.

Network 104 may include one or more wired and/or wireless networks. For example, network 104 may include a cellular network (e.g., a long-term evolution (LTE) network, a third generation (3G) network, a fourth generation (4G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, a short range wireless communication network (e.g., a Bluetooth network, a near field communication (NFC) network, etc.) and/or the like, and/or a combination of these or other types of networks.

The number and arrangement of systems, devices, and networks shown in FIGS. 1A-1E are provided as an example. There may be additional systems, devices, and/or networks, fewer systems, devices, and/or networks, different systems, devices, and/or networks, or differently arranged systems, devices, and/or networks than those shown in FIGS. 1A-1E, Furthermore, two or more systems or devices shown in FIGS. 1A-1E may be implemented within a single system or a single device, or a single system or a single device shown in FIGS. 1A-1E may be implemented as multiple, distributed systems or devices. Additionally, or alternatively, a set of systems or a set of devices (e.g., one or more systems, one or more devices, etc.) of environment 100 may perform one or more functions described as being performed by another set of systems or another set of devices of environment 100.

Figure 2:
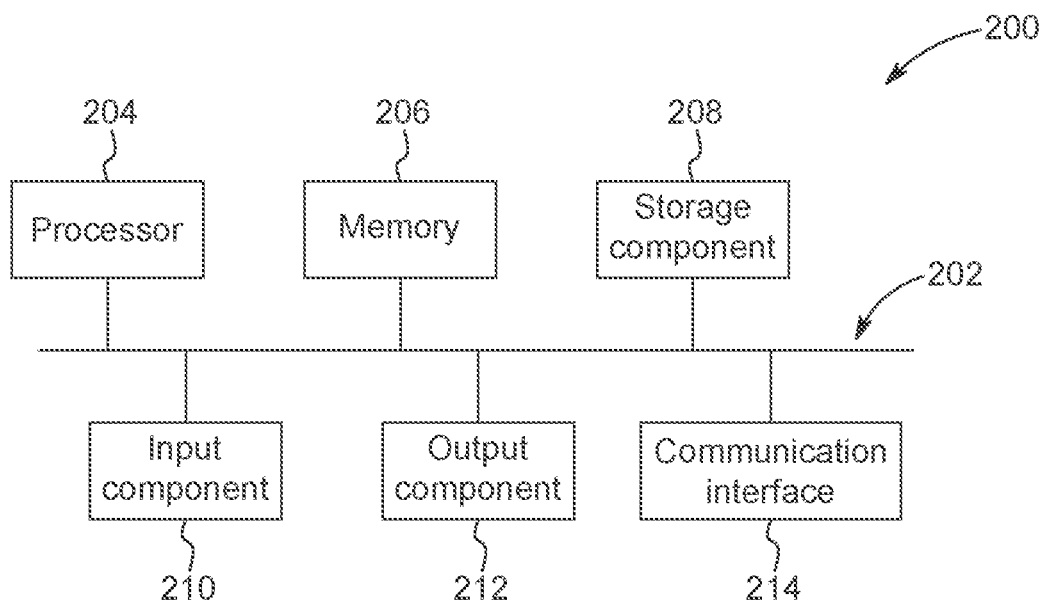
FIG. 2 is a diagram of a non-limiting embodiment or aspect of components of one or more systems or one or more devices of FIGS. 1A-1E.

Referring now to FIG. 2, FIG. 2 is a diagram of example components of a device 200. Device 200 may correspond to one or more devices of the plurality of injection systems 102 (e.g., one or more devices of injection system 102a, one or more devices of injection system 102b, one or more devices of injection system 102c, etc.). In some non-limiting embodiments or aspects, the plurality of injection systems 102 (e.g., first injection system 102a, second injection system 102b, third injection system 102c, etc.) can include at least one device 200 and/or at least one component of device 200. As shown in FIG. 2, device 200 may include a bus 202, a processor 204, memory 206, a storage component 208, an input component 210, an output component 212, and a communication interface 214.

Bus 202 may include a component that permits communication among the components of device 200. In some non-limiting embodiments or aspects, processor 204 may be implemented in hardware, firmware, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210 may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214, When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein, Thus, embodiments or aspects described herein are not limited to any specific combination of hardware circuitry and software.

The number and arrangement of components shown in FIG. 2 are provided as an example. In some non-limiting embodiments or aspects, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
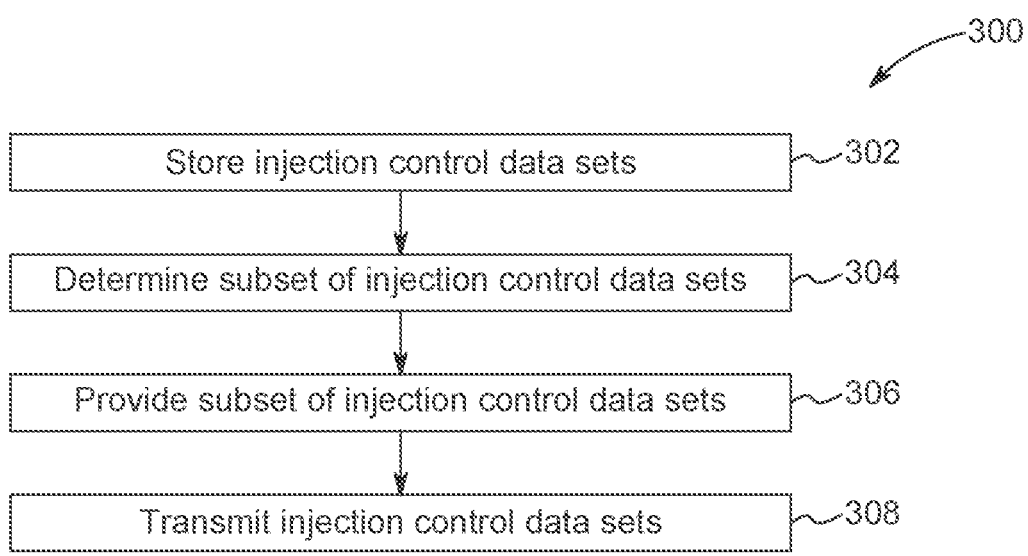
FIG. 3 is a flowchart of a non-limiting embodiment or aspect of a process for peer exchange of data between injection systems.

Referring now to FIG. 3, FIG. 3 is a flowchart of a non-limiting embodiment or aspect of a process 300 for peer exchange of data between injection systems. In some non-limiting embodiments or aspects, one or more of the steps of process 300 may be performed (e.g., completely, partially, etc.) by one or more injection systems of the plurality of injection systems 102 (e.g., first injection system 102a, second injection system 102b, third injection system 102c, etc.). For example, one or more of the steps of process 300 may be performed (e.g., completely, partially, etc.) by first injection system 102a (e.g., one or more devices of first injection system 102a). In some non-limiting embodiments or aspects, one or more of the steps of process 300 may be performed (e.g., completely, partially, etc.) by another device or a group of devices separate from or including first injection system 102a, such as second injection system 102b (e.g., one or more devices of second injection system 102b) and/or third injection system 102c (e.g., one or more devices of third injection system 102c).

As shown in FIG. 3, at step 302, process 300 includes storing a plurality of injection control data sets. For example, one or more injection systems of the plurality of injection systems 102 stores a plurality of injection control data sets (e.g., a plurality of injection protocols, a plurality of presets, etc.). In such an example, first injection system 102a can store the plurality of injection control data sets. For example, first injection system 102a can store each injection control data set of a plurality of injection control data sets for each injection system (e.g., first injection system 102a, second injection system 102b, third injection system 102c, etc.) of the plurality of injection systems 102. As an example, second injection system 102b (and/or third injection system 102c, etc.) can store a plurality of injection control data sets. In such an example, second injection system 102b (and/or third injection system 102c, etc.) can store each injection control data set of a plurality of injection control data sets for each injection system (e.g., first injection system 102a, second injection system 102b, third injection system 102c, etc.) of the plurality of injection systems 102.

In some non-limiting embodiments or aspects, the plurality of injection systems 102 includes a plurality of different types of injection systems (e.g. injection systems from different manufacturers, different models of injection systems, different versions of a same model of injection system, etc.), and one or more injection control data sets (e.g., one or more injection protocols, one or more presets, etc.) of the plurality of injection control data sets are programmed or configured for one or more injection systems of the plurality of different types of injection systems. For example, one or more injection systems of the plurality of injection systems 102 (e.g., first injection system 102a, etc.) can include a first type of injection system, one or more other injection systems of the plurality of injection systems 102 (e.g., second injection system 102b, etc.) can include a second type of injection system, and the first type of injection system can be different than the second type of injection system. As an example, one or more injection systems of the plurality of injection systems 102 (e.g., first injection system 102a, a first type of injection system, etc.) can be programmed or configured to control delivery of and/or to deliver fluid to a patient based on a first subset of the plurality of injection control data sets, one or more other injection systems of the plurality of injection systems (e.g., second injection system 102b, a second type of injection system, etc.) can be programmed or configured to control delivery of and/or to deliver fluid to a patient based on a second subset of the plurality of injection control data sets, and the second subset can include at least one injection control data set (e.g., at least one injection protocol, at least one preset, etc.) different than the first subset. As an example, the one or more injection systems (e.g., first injection system 102a) may not be programmed or configured to control delivery of and/or to deliver fluid to a patient based on the at least one different injection control data set not included in the first subset of injection control data sets (e.g., the at least one different injection control data set cannot be installed, initiated, and/or executed by first injection system 102a and/or the first type of injection system); however, the one or more other injection systems (e.g., second injection system 102b) may be programmed or configured to control delivery of and/or to deliver fluid to a patient based on the at least one different injection control data set included in the second subset of injection control data sets (e.g., the at least one different injection control data set can be installed, initiated, and/or executed by second injection system 102b and/or the second type of injection system).

In some non-limiting embodiments or aspects, the plurality of injection control data sets include a plurality of different injection control data sets that vary according to one or more parameters of the injection control data sets (e.g., according to one or more parameters of injection protocols, one or more parameters of presets, etc.) and/or one or more types of injection systems for which the injection control data sets are programmed or configured. However, in some non-limiting embodiments or aspects, each of the injection systems of the plurality of injection systems 102 stores or is capable of storing each of the injection control data sets of the plurality of injection control data sets for the plurality of injection systems 102. For example, one or more injection systems of the plurality of injection systems 102 (e.g., first injection system 102a, etc.) can store one or more injection control data sets (e.g., at least one injection control data set not included in the first subset of the plurality of injection control data sets for first injection system 102a) for which the one or more injection systems are not programmed or configured to control delivery of and/or to deliver fluid to a patient (e.g., an injection control data set that cannot be installed, initiated, and/or executed by first injection system 102a and/or the first type of injection system).

As further shown in FIG. 3, at step 304, process 300 includes determining a subset of the plurality of injection control data sets according to which at least one injection system is configured to control delivery of fluid to a patient. For example, one or more injection systems of the plurality of injection systems 102 determines one or more subsets of the plurality of injection control data sets (e.g., one or more subsets of the plurality of injection protocols, one or more subsets of the plurality of presets, etc.) according to which the one or more injection systems is configured to control delivery of fluid to a patient. In such an example, first injection system 102a determines a first subset of the plurality of injection control data sets according to which first injection system 102a is programmed or configured to deliver fluid to a patient. As an example, first injection system 102a determines at least one injection control data set of the plurality of injection control data sets that can be installed, initiated, and/or executed by first injection system 102a to deliver fluid to a patient, and/or first injection system 102a determines a remainder of the plurality of injection control data sets that cannot be installed, initiated, and/or executed by first injection system 102a to deliver fluid to a patient. In such an example, second injection system 102b (and/or third injection system 102c, etc.) determines a second subset (and/or a third subset, etc.) of the plurality of injection control data sets according to which second injection system 102b (and/or third injection system 102c, etc.) is configured to deliver fluid to a patient. As an example, second injection system 102b (and/or third injection system 102c, etc.) determines at least one subset of the plurality of injection control data sets that can be installed, initiated, and/or executed by second injection system 102b (and/or third injection system 102c, etc.) to deliver fluid to a patient; and/or second injection system 102b (and/or third injection system 102c, etc.) determines a remainder of the plurality of injection control data sets that cannot be installed, initiated, and/or executed by second injection system 102b (and/or third injection system 102c, etc.) to deliver fluid to a patient.

In some non-limiting embodiments or aspects, first injection system 102a can be programmed or configured to control delivery of and/or to deliver fluid to a patient based on the first subset of the plurality of injection control data sets, second injection system 102b can be programmed or configured to control delivery of and/or to deliver fluid to a patient based on the second subset of the plurality of injection control data sets, third injection system 102c can be programmed or configured to control delivery of and/or to deliver fluid to a patient based on the third subset of the plurality of injection control data sets, etc.; and the first subset, the second subset and the third subset may include at least one injection control data set (e.g., at least one injection protocol, at least one preset, etc.) different from each other. For example, the second subset can include at least one injection control data set different than the first subset, the first subset can include at least one injection control data set different than the third subset, and the third subset can include at least one injection control data set different than the second subset.

As further shown in FIG. 3, at step 306, process 300 includes providing the subset of the plurality of injection control data sets for selection of an injection control data set for use in delivering fluid to a patient with the at least one injection system. For example, one or more injection systems of the plurality of injection systems 102 provides the one or more subsets of the plurality of injection control data sets (e.g., the one or more subsets of the plurality of injection protocols, the one or more subsets of the plurality of presets, eta) for selection of an injection control data set (e.g., for selection of an injection protocol, for selection of a preset, etc.) for use in delivering fluid to a patient with the one or more injection systems. In such an example, first injection system 102a provides the first subset of the plurality of injection control data sets (e.g., provides the first subset of the plurality of injection control data sets at first injection system 102a, etc.) for selection of an injection control data set for delivering fluid to a patient with first injection system 102a. As an example, first injection system 102a provides the first subset of the plurality of injection control data sets (e.g., outputs the first subset, enables the injection system to be programmed or configured to deliver fluid according to the first subset, etc.) for delivering fluid to a patient with first injection system 102a via output component 212 (e.g., via a display, etc.) to a user. In such an example, second injection system 102b (and/or third injection system 102c, etc.) provides the second subset (and/or the third subset, etc.) of the plurality of injection control data sets for delivering fluid to a patient with second injection system 102b (and/or third injection system 102c, etc.). As an example, second injection system 102b (and/or third injection system 102c, etc.) provides the second subset of the plurality of injection control data sets for delivering fluid to a patient with second injection system 102b (and/or third injection system 102c, etc.) via output component 212 (e.g., via a display, etc.) to a user.

In some non-limiting embodiments or aspects, first injection system 102a (and/or second injection system 102b, third injection system 102c, etc.) provides the first subset (and/or the second subset, the third subset, etc.) of the plurality of injection control data sets to the user without providing the remainder of the plurality of injection control data sets to the user. For example, first injection system 102a displays the at least one injection control data set (e.g., in a list of available injection control data sets; in a list of the corresponding subset of injection control data sets, etc.) of the plurality of injection control data sets that can be installed, initiated, and/or executed by first injection system 102a to deliver fluid to a patient, but first injection system 102a does not display the remainder of the plurality of injection control data sets that cannot be installed; initiated; and/or executed by first injection system 102a to deliver fluid to a patient (e.g., the injection protocols and/or presets that cannot be installed, initiated, and/or executed by first injection system 102a to deliver fluid to a patient). In some non-limiting embodiments or aspects, first injection system 102a (and/or second injection system 102b, third injection system 102c, etc.) prompts the user to provide a selection of an injection control data set (e.g., a selection of an injection protocol; a selection of a preset, etc.) from the first subset (and/or the second subset, the third subset; etc.) of the plurality of injection control data sets (e.g., from the list of available injection control data sets, etc.) for delivering fluid to a patient with first injection system 102a. For example, first injection system 102 prompts the user to provide a selection of an injection control data set from the first subset for delivering fluid to a patient with first injection system 102a.

In some non-limiting embodiments or aspects, one or more injection systems of the plurality of injection systems 102 receives at least one of (i) accessory data associated with a plurality of catheters and (ii) fluid data associated with a plurality of fluids. For example, first injection system 102a (and/or second injection system 102b; third injection system 102c, etc.) receives the accessory data and/or the fluid data from another injection system in a peer-to-peer network of the plurality of injection systems 102 and/or retrieves the accessory data and/or the fluid data from a database. As an example, one or more injection systems of the plurality of injection systems 102 can automatically transmit an update to the accessory data and/or the fluid data to other injection systems in the peer-to-peer network of the plurality of injection systems 102 in response to a change in the accessory data and/or the fluid data at the one or more injection systems of the plurality of injection systems 102. In such an example, one or more injection systems of the plurality of injection systems 102 can receive a selection of the injection control data set for use in delivering fluid to a patient. For example, first injection system 102a (and/or second injection system 102b, third injection system 102c, etc.) receives a selection of the injection control data set for use in delivering fluid to the patient with first injection system 102a (and/or second injection system 102b, third injection system 102c, etc.). The one or more injection systems of the plurality of injection systems 102 may determine at least one of (i) a subset of the plurality of catheters for use in delivering the at least one fluid to the patient and (ii) a subset of the plurality of fluids for use in delivering the at least one fluid to the patient, based on the selected injection control data set. For example, first injection system 102a (and/or second injection system 102b, third injection system 102c, etc.) determines at least one of (i) a subset of the plurality of catheters for use in delivering the at least one fluid to the patient and (ii) a subset of the plurality of fluids for use in delivering the at least one fluid to the patient, based on the selected injection control data set. As an example, a number and/or type of catheters and/or a number and/or type of fluids available for use in delivering fluid to the patient may be dependent on the selected injection control data set (e.g., the selected injection control data set may specify a certain type(s) of catheter and/or a certain type(s) of fluids that can be used to deliver fluid with the selected injection control data set). In such an example, the one or more injection systems of the plurality of injection systems 102 can provide the at least one of (i) the subset of the plurality of catheters, for selection of a catheter for using in delivering the at least one fluid to the patient, and (ii) the subset of the plurality of fluids, for selection of a fluid for use in delivering the at least one fluid to the patient. For example, first injection system 102a (and/or second injection system 102b, third injection system 102c, etc.) can display a list of the subset of the plurality of catheters, for selection of a catheter for using in delivering the at least one fluid to the patient, and/or a list of the subset of the plurality of fluids, for selection of a fluid for use in delivering the at least one fluid to the patient. As an example, first injection system 102a (and/or second injection system 102b, third injection system 102c, etc.) can receive a selection of a catheter and/or a selection of a fluid for use in delivering the at least one fluid to the patient.

Further details regarding step 306 of process 300 are provided below with regard to FIG. 4.

As further shown in FIG. 3, at step 308, process 300 includes transmitting the plurality of injection control data sets to at least one other injection system. For example, one or more injection systems of the plurality of injection systems 102 transmits the plurality of injection control data sets (e.g., the plurality of injection protocols, the plurality of presets, etc.) to one or more other injection systems of the plurality of injection systems 102. In such an example, first injection system 102a transmits the plurality of injection control data sets to second injection system 102a (and/or third injection system 102c, etc.). For example, first injection system 102a transmits each injection control data set of a plurality of injection control data sets for each injection system (e.g., first injection system 102a, second injection system 102b, third injection system 102c, etc.) of the plurality of injection systems 102 to second injection system 102a (and/or third injection system 102c, etc.). As an example, second injection system 102b (and/or third injection system 102c, etc.) receives the plurality of injection control data sets from first injection system 102a. For example, second injection system 102b (and/or third injection system 102c, etc.) receives each injection control data set of a plurality of injection control data sets for each injection system (e.g., first injection system 102a, second injection system 102b, third injection system 102c, etc.) of the plurality of injection systems 102 from first injection system 102a. In such an example, second injection system 102b transmits the plurality of injection control data sets to third injection system 102c (and/or first injection system 102a, etc.). For example, second injection system 102b transmits each injection control data set of a plurality of injection control data sets for each injection system (e.g., first injection system 102a, second injection system 102b, third injection system 102c, etc.) of the plurality of injection systems 102 to third injection system 102c (and/or first injection system 102a, etc.). As an example, third injection system 102c (and/or first injection system 102a, etc.) receives the plurality of injection control data sets from second injection system 102b. For example, third injection system 102c (and/or first injection system 102a, etc.) receives each injection control data set of a plurality of injection control data sets for each injection system (e.g., first injection system 102a, second injection system 102b, third injection system 102c, etc.) of the plurality of injection systems 102 from second injection system 102b.

In some non-limiting embodiments or aspects, the one or more injection systems of the plurality of injection systems 102 periodically transmits (e.g., transmits each hour, each day, each week, each month, etc.) the plurality of injection control data sets to the one or more other injection systems of the plurality of injection systems 102. In some non-limiting embodiments or aspects, the one or more injection systems of the plurality of injection systems 102 transmits the plurality of injection control data sets to the one or more other injection systems of the plurality of injection systems 102 in response to a change in one or more of injection control data sets (e.g., a change in one or more parameters of one or more injection protocols, a change in one or more parameters of one or more presets, eta) at the one or more injection systems. In such an example, first injection system 102a transmits the plurality of injection control data sets in response to a creation of a new injection control data set, an update to an existing injection control data set (e.g., for new equipment, etc.), a modification to an existing injection control data set, and/or a deletion of an existing injection control data set that occurs at first injection system 102a.

Further details regarding step 308 of process 300 are provided below with regard to FIG. 5.

Figure 4:
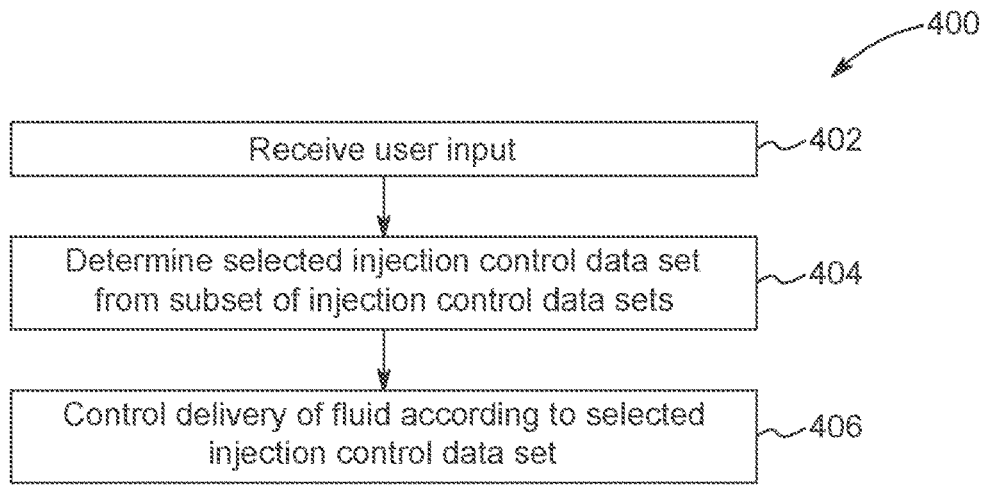
FIG. 4 is a flowchart of a non-limiting embodiment or aspect of a process for peer exchange of data between injection systems.

Referring now to FIG. 4, FIG. 4 is a flowchart of a non-limiting embodiment or aspect of a process 400 for peer exchange of data between injection systems. In some non-limiting embodiments or aspects, one or more of the steps of process 300 may be performed (e.g., completely, partially, etc.) by one or more injection systems of the plurality of injection systems 102 (e.g., first injection system 102a, second injection system 102b, third injection system 102c, etc.). For example, one or more of the steps of process 300 may be performed (e.g., completely, partially, etc.) by first injection system 102a (e.g., one or more devices of first injection system 102a). In some non-limiting embodiments or aspects, one or more of the steps of process 300 may be performed (e.g., completely, partially, etc.) by another device or a group of devices separate from or including first injection system 102a, such as second injection system 102b (e.g., one or more devices of second injection system 102b) and/or third injection system 102c (e.g., one or more devices of third injection system 102c).

As shown in FIG. 4, at step 402, process 400 includes receiving user input. For example, one or more injection systems of the plurality of injection systems 102 receives user input. In such an example, first injection system 102a receives user input. As an example, first injection system 102a receives user input via input component 210 in response to prompting the user to provide a selection of an injection control data set from the first subset of the plurality of injection control data sets (e.g., from the list of available injection control data sets, etc.) for delivering fluid to a patient with first injection system 102a. In such an example, second injection system 102b (and/or third injection system 102c, etc.) receives user input. As an example, second injection system 102b (or third injection system 102c, etc.) receives user input via input component 210 in response to prompting the user to provide a selection of an injection control data set from the second subset (or third subset, etc.) of the plurality of injection control data sets (e.g., from the list of available injection control data sets, etc.) for delivering fluid to a patient with second injection system 102b (or third injection system 102c, etc.).

In-some non-limiting embodiments or aspects, one or more injection systems of the plurality of injection systems 102 receives a selection of an injection control data set (e.g., a selection of an injection protocol, a selection of a preset, etc.) from the one or more subsets of the plurality of injection control data sets. In such an example, first injection system 102a receives a selection (e.g., a direct identification, etc.) of an injection control data set from the first subset of the plurality of injection control data sets. In such an example, second injection system 102b (or third injection system 102c, etc.) receives a selection (e.g., a direct identification, etc.) of an injection control data set from the second subset (or the third subset, etc.) of the plurality of injection protocols.

In some non-limiting embodiments or aspects, one or more injection systems of the plurality of injection systems 102 receives patient data associated with a patient (e.g., age, weight, height, body mass index (BMI), cardiac output, a procedure to be performed, etc.) and/or one or more desired parameters (e.g., flow rate, etc.) of the injection control data set (e.g., of the injection protocol, of the preset, etc.) and determines a selected injection control data set for use in delivering the fluid to the patient from the one or more subsets of the plurality of injection control data sets based on the patient data and/or the one or more desired parameters of the injection control data set. In such an example, first injection system 102a receives patient data associated with the patient (e.g., age, weight, height, body mass index (BMI), cardiac output, a procedure to be performed, etc.) and/or one or more desired parameters (e.g., flow rate, etc.) of the injection control data set and determines a selected injection control data set for delivering the fluid to the patient from the first subset of the plurality of injection control data sets based on the patient data associated with the patient and/or the one or more desired parameters of the injection control data set. In such an example, second injection system 102b (or third injection system 102c, etc.) receives patient data associated with the patient and/or one or more desired parameters of the injection control data set and determines a selected injection control data set for delivering the fluid to the patient from the second subset (or third subset, etc.) of the plurality of injection control data sets based on the patient data associated with the patient and/or the one or more desired parameters of the injection control data set. For example, a selected injection protocol can include contrast agent protocols described in U.S. Pat. Nos. 6,055,985 and 6,635,030, both to Bae et al., which describe a methodology for determining a protocol for delivering a contrast agent to a patient which attempts to optimize the use of contrast agent to achieve an enhancement in excess of a preselected threshold and to maintain that excess level of enhancement for a temporal duration that is near optimal given the amount of contrast used, the entire contents of each of which are incorporated herein by reference.

As further shown in FIG. 4, at step 404, process 400 includes determining a selected injection control data set for delivering the fluid to the patient from the subset of the plurality of injection control data sets based on the user input. For example, one or more injection systems of the plurality of injection systems 102 determines a selected injection control data set for delivering the fluid to the patient from the one or more subsets of the plurality of injection control data sets based on the user input. In such an example, first injection system 102a determines a selected injection control data set for delivering the fluid to the patient from the first subset of the plurality of injection control data sets based on the user input. In such an example, second injection system 102b (or third injection system 102c, etc.) determines a selected injection control data set for delivering the fluid to the patient from the second subset (or the third subset, etc.) of the plurality of injection control data sets based on the user input.

As further shown in FIG. 4, at step 406, process 400 includes controlling delivery of the fluid to the patient according to the selected injection control data set. For example, the one or more injection systems of the plurality of injection systems 102 controls delivery of and/or delivers the fluid to the patient according to the selected injection control data set. In such an example, first injection system 102a delivers the fluid to the patient according to the selected injection control data set determined from the first subset of the plurality of injection control data sets. As an example, first injection system 102a delivers a contrast agent via a bolus injection according to the selected injection control data set. In such an example, second injection system 102b (or third injection system 102c, etc.) delivers the fluid to the patient according to the selected injection control data set determined from the second subset (or the third subset, etc.) of the plurality of injection control data sets. As an example, second injection system 102b (or third injection system 102c, etc.) delivers a contrast agent via a bolus injection according to the selected injection control data set.

In some non-limiting embodiments or aspects, an imaging system performs imaging (e.g., positron emission tomography (PET) imaging, computed tomography (CT) imaging, magnetic resonance (MR) imaging, single-photon emission computed tomography (SPECT) imaging, etc.) of the patient based on the selected injection control data set (e.g., to start imaging according to the selected injection control data set, etc.). For example, one or more injection systems of the plurality of injection systems 102 controls an imaging system to perform imaging of the patient before, during, and/or after delivering the fluid to the patient according to the selected injection control data set.

Figure 5:
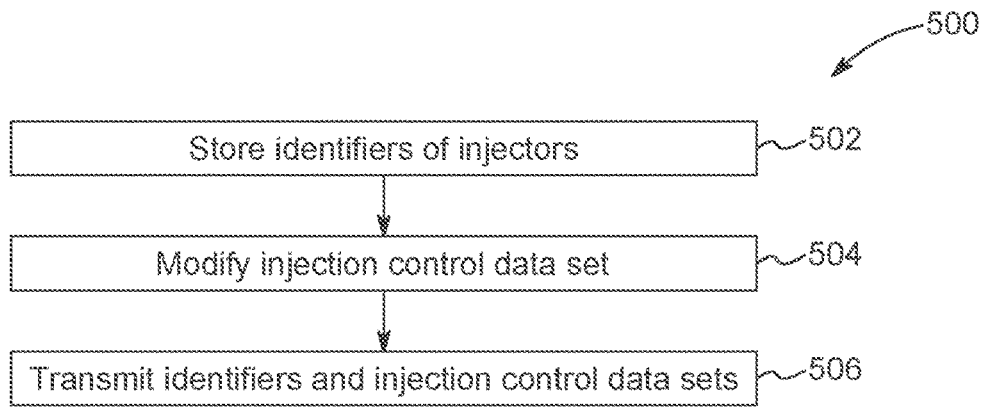
FIG. 5 is a flowchart of a non-limiting embodiment or aspect of a process for peer exchange of data between injection systems.

Referring now to FIG. 5, FIG. 5 is a flowchart of a non-limiting embodiment or aspect of a process 500 for peer exchange of data between injection systems. In some non-limiting embodiments or aspects, one or more of the steps of process 300 may be performed (e.g., completely, partially, etc.) by one or more injection systems of the plurality of injection systems 102 (e.g., first injection system 102a, second injection system 102b, third injection system 102c, etc.). For example, one or more of the steps of process 300 may be performed (e.g., completely, partially, etc.) by first injection system 102a (e.g., one or more devices of first injection system 102a). In some non-limiting embodiments or aspects, one or more of the steps of process 300 may be performed (e.g., completely, partially, etc.) by another device or a group of devices separate from or including first injection system 102a, such as second injection system 102b (e.g., one or more devices of second injection system 102b) and/or third injection system 102c (e.g., one or more devices of third injection system 102c).

As shown in FIG. 5, at step 502, process 500 includes storing a plurality of identifiers associated with a plurality of injection systems. For example, one or more injection systems of the plurality of injection systems 102 store a plurality of identifiers associated with the plurality of injection systems 102. In such an example, first injection system 102a stores a plurality of identifiers associated with a plurality of injection systems including first injection system 102a, second injection system 102b, third injection system 102c, etc. In such an example, second injection system 102b (and/or third injection system 102c, etc.) stores a plurality of identifiers associated with a plurality of injection systems including first injection system 102a, second injection system 102b, third injection system 102c, etc. As an example, one or more injection systems (e.g., first injection system 102a, second injection system 102b, third injection system 102c, etc.) of the plurality of injection systems can be associated with a unique identifier that uniquely identifies the one or more injection systems among the plurality of injection systems 102, and the unique identifier of that injection system can be associated with one or more injection control data sets of the plurality of injection control data sets according to which that injection system can be programmed or configured to deliver fluid to a patient. In some non-limiting embodiments or aspects, each injection system of the plurality of injection systems 102 stores or is capable of storing a unique identifier for each injection system of the plurality of injection systems 102 (e.g., a unique identifier for each injection system included in a peer-to-peer network of the plurality of injection systems 102, etc.).

As further shown in FIG. 5, at step 504, process 500 includes modifying one or more injection control data sets of the plurality of injection control data sets. For example, one or more injection systems of the plurality of injection systems 102 modifies (e.g., creates a new injection control data set, provides updates to an existing injection control data set (e.g., for new equipment, etc.), modifies parameters of an existing injection control data set, deletes an existing injection control data set, etc.) the one or more injection control data sets of the plurality of injection control data sets. In such an example, first injection system 102a modifies one or more injection control data sets of the plurality of injection control data sets at first injection system 102a. In such an example, second injection system 102b (and/or third injection system 102c, etc.) modifies one or more injection control data sets of the plurality of injection control data sets at second injection system 102b (and/or third injection system 102c, eta). In some non-limiting embodiments or aspects, the one or more injection control data sets are associated with at least one other injection system. As an example, first injection system 102a modifies one or more injection control data sets of the plurality of injection control data sets at first injection system 102a that are associated with at least one identifier of third injection system 102c.

As further shown in FIG. 5, at step 506, process 500 includes transmitting the plurality of identifiers. For example, one or more injection systems of the plurality of injection systems 102 transmits the plurality of identifiers to one or more other injection systems of the plurality of injection systems 102. In some non-limiting embodiments or aspects, the one or more injection systems of the plurality of injection systems 102 transmits the plurality of identifiers in association with the plurality of injection control data sets. As an example, identifiers of injection systems of the plurality of injection systems 102 that are programmed or configured to deliver fluid to a patient according to one or more injection control data sets of the plurality of injection control data sets can be associated with those one or more injection control data sets. In such an example, first injection system 102a transmits the plurality of identifiers (e.g., identifiers of first injection system 102a, second injection system 102b, third injection system 102c, etc.) and/or the plurality of injection control data sets to second injection system 102b (and/or third injection system 102c, etc.). As an example, second injection system 102b stores (e.g., updates a database of, etc.) the plurality of identifiers and the plurality of injection control data sets in response to receiving the plurality of identifiers and the plurality of injection control data sets from first injection system 102a. In such an example, second injection system 102b transmits the plurality of identifiers to third injection system 102c (and/or first injection system 102a, etc.). As an example, third injection system 102c stores (e.g., updates a database of, etc.) the plurality of identifiers and the plurality of injection control data sets in response to receiving the plurality of identifiers and the plurality of injection control data sets from second injection system 102b.

Although steps 504 and 506 in process 500 are described with respect to modifying one or more injection control data sets, non-limiting embodiments or aspects are not limited thereto, and one or more injection systems of the plurality of injection systems 102 may receive, store, and/or modify any type of data and/or information described herein (e.g., injection control data, patient data, injection system settings data, fluid data, accessory data, preset data, prior exam data, etc.). As an example, a number and/or type of catheters available at an imaging site, an amount and/or type of fluids available at the imaging site, and/or configuration settings of an individual injection system can be modified or updated at the individual injection system of the plurality of injection systems 102. In such an example, the individual injection system can directly transmit the modified or updated data to at least one other injection system in the peer-to-peer network including the plurality of injection systems 102. For example, the individual injection system can automatically transmit, in response to modifying the data, (e.g., without receiving a request or query for the data, etc.) the modified data to at least one other injection system in the peer-to-peer network including the plurality of injection systems. Accordingly, other injection systems in the peer-to-peer network, which may be unaware that the data has been modified, can be more quickly updated with the modified data, without having to continuously query the injection system for any updates or modifications.

In some non-limiting embodiments or aspects, one or more injection systems of the plurality of injection systems 102 manages membership of injection systems of the plurality of injection systems 102 in a peer-to-peer network based on the plurality of identifiers (e.g., a plurality of IP addresses, etc.). For example, one or more injection systems of the plurality of injection systems 102 may maintain a list of identifiers that includes identifiers of injection systems that are members of the peer-to-peer network. As an example, one or more injection systems of the plurality of injection systems 102 may transmit modifications or updates of data and/or information (e.g., injection control data, patient data, injection system settings data, fluid data, accessory data, preset data, prior exam data, etc.) and/or network member peer-to-peer network membership statuses to other injection systems based on the list of identifiers. In such an example, the plurality of injection systems 102 may perform a conflict detection and resolution function for data within the peer-to-peer network based on the plurality of identifiers. For example, one or more injection systems of the plurality of injection systems 102 can determine a type of an injection system, a version of (and/or a compatibility of) an application on an injection system, and/or the like based on the identifier associated with that injection system, and the one or more injection systems can select an application or protocol for communicating with and/or updating that injection system based on the identifier.

Figure 6:
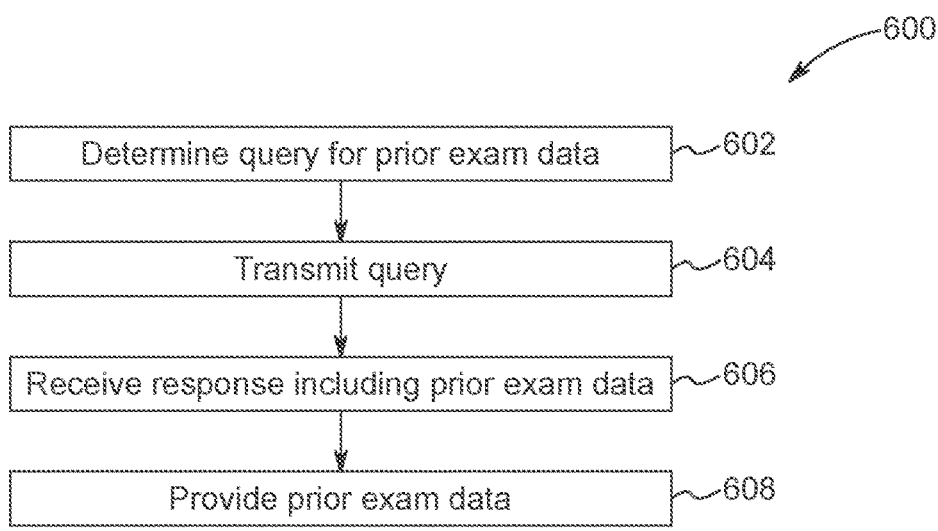
FIG. 6 is a flowchart of a non-limiting embodiment or aspect of a process for peer exchange of data between injection systems.

Referring now to FIG. 6, FIG. 6 is a flowchart of a non-limiting embodiment or aspect of a process 600 for peer exchange of data between injection systems. In some non-limiting embodiments or aspects, one or more of the steps of process 600 may be performed (e.g., completely, partially, etc.) by one or more injection systems of the plurality of injection systems 102 (e.g., first injection system 102*a*, second injection system 102*b*, third injection system 102*c*, etc.). For example, one or more of the steps of process 600 may be performed (e.g., completely, partially, etc.) by first injection system 102*a* (e.g., one or more devices of first injection system 102*a*). In some non-limiting embodiments or aspects, one or more of the steps of process 600 may be performed (e.g., completely, partially, etc.) by another device or a group of devices separate from or including first injection system 102*a*, such as second injection system 102*b* (e.g., one or more devices of second injection system 102*b*) and/or third injection system 102*c* (e.g., one or more devices of third injection system 102*c*).

As shown in FIG. 6, at step 602, process 600 includes determining a query for prior exam data associated with a patient. For example, an injection system in a peer-to-peer network including the plurality of injection systems 102 determines a query for prior exam data associated with a patient. As an example, the injection system can determine the query based on user input and/or data associated with the patient and/or a procedure to be performed at the injection system. In such an example, a user may input a query to the injection system to search other injection systems in the peer-to-peer network for prior exam data associated with the patient (e.g., associated with a unique patient identifier, etc.) and/or a particular exam or type of exam (e.g., a unique exam identifier, an identifier of a type of exam, etc.).

As further shown in FIG. 6, at step 604, process 600 includes transmitting the query to at least one other injection system in the peer-to-peer network including the plurality of injection systems 102. For example, the injection system in the peer-to-peer network including the plurality of injection systems 102 transmits the query to at least one other injection system in the peer-to-peer network including the plurality of injection systems. As an example, the injection system directly transmits the query to the at least one other injection system in the peer-to-peer network via logical connections or a virtual overlay network between the injection systems.

As further shown in FIG. 6, at step 606, process 600 includes receiving a response to the query from the at least one other injection system in the peer-to-peer network. For example, the injection system in the peer-to-peer network including the plurality of injection systems 102 receives a response to the query from the at least one other injection system in the peer-to-peer network of the plurality of injection systems 102.

In some non-limiting embodiments or aspects, the response to the query includes the prior exam data, and the prior exam data includes at least one record associated with at least one prior exam performed on the patient. For example, the at least one record may include at least one of the following: (a) patient data associated with the patient, (b) an injection control data set according to which at least one fluid was injected into the patient during the at least one prior exam, (c) injection system settings data associated with the at least one other injection system at which the at least one prior exam was performed, (d) accessory data associated with a type of catheter through which the at least one fluid was injected into the patient during the at least one prior exam, (e) procedure data associated with an injection site on the patient at which the catheter was located during the at least one prior exam, or any combination thereof. In some non-limiting embodiments or aspects, the at least one record comprises a plurality of records associated with a plurality of prior exams performed on the patient at the at least one other injection system in the peer to peer network of the plurality of injection systems 102. For example, the plurality of records may include a plurality of injection control data sets according to which the at least one fluid was injected into the patient during a plurality of prior exams.

In some non-limiting embodiments or aspects, the patient data includes at least one of the following parameters associated with the patient: (i) a first name of the patient, (ii) a last name of the patient, (iii) a weight of the patient, (iv) a height of the patient, (v) a gender of the patient, (vi) a date of birth of the patient, (vii) a unique identifier of the patient, or any combination thereof.

In some non-limiting embodiments or aspects, the injection control data set includes an injection protocol including at least one of the following parameters according to which the at least one fluid was injected into the patient during the at least one prior exam: (i) a volume of a first fluid of the at least one fluid programmed to be injected into the patient, (ii) a volume of a second fluid of the at least one fluid programmed to be injected into the patient, (iii) a volume of the first fluid of the at least one fluid injected into the patient during the at least one prior exam, (iv) a volume of the second fluid of the at least one fluid injected into the patient during the at least one prior exam, (v) a flow rate at which the first fluid of the at least one fluid was programmed to be injected into the patient, (vi) a flow rate at which the second fluid of the at least one fluid was programmed to be injected into the patient, (vii) a flow rate at which the first fluid of the at least one fluid was injected into the patient during the at least one prior exam, (viii) a flow rate at which the second fluid of the at least one fluid was injected into the patient during the at least one prior exam; (ix) a pressure threshold defining a maximum pressure generated via the at least one fluid within the at least one other injection system during the prior injection, (x) a start time for the prior injection, and (xi) an end time for the prior injection, or any combination thereof.

In some non-limiting embodiments or aspects, the injection system settings data includes at least one of the following parameters associated with a configuration of the at least one other injection system at which the at least one prior exam is performed: (i) a unit of weight measure used by the injection system, (ii) a unit of pressure used by the injection system, (iii) a language used by the injection system; (iv) a date selected as a reminder to calibrate the injection system, (v) a volume selected for audio provided by the injection system, (vi) a current date and/or time used by the injection system, (vii) a format for the date used by the injection system, (viii) a format for the time used by the injection system, (ix) a setting indicative of an availability of injector-scanner interfacing (ISI), or any combination thereof.

As further shown in FIG. 6, at step 608, process 600 includes providing the prior exam data via a user interface. For example, the injection system in the peer-to-peer network including the plurality of injection systems 102 provides the prior exam data via a user interface (e.g., via output component 212, etc.). As an example, FIG. 7 shows an implementation of a display of prior exam data (e.g., a record of an exam for a patient at an injection system) provided by a non-limiting embodiment or aspect of an injection system of the plurality of injection systems 102.

In some non-limiting embodiments or aspects, the injection system in the peer-to-peer network including the plurality of injection systems 102 determines an injection control data set for use in delivering at least one fluid to the patient with the injection system based on the at least one record. For example, the injection system can determine the injection control data set based on user input and/or data associated with the patient and/or a procedure to be performed at the injection system. In such an example, the injection control system can determine the injection control data set based on the prior exam data as described by the U.S. Patents to Bae et al. incorporated by reference herein above. In such an example, a user may select the injection control data set (e.g.; injection protocol, preset, etc.) from a list of injection control data sets provided by the injection system via the user interface.

The invention claimed is:

1. A computer-implemented method for peer exchange of data between injection systems comprising:
storing, with at least one first injection system, a plurality of unique identifiers associated with a plurality of injection systems including the at least one first injection system, at least one second injection system, and at least one third injection system, wherein the plurality of injection systems includes a peer-to-peer network of injection systems formed by the plurality of injection systems implementing a virtual overlay network on top of a physical network topology;
storing, with the at least one first injection system, a plurality of injection control data sets, wherein each unique identifier is associated with at least one injection control data set of the plurality of injection control data sets including parameters according to which an injection system associated with the unique identifier is configured to be programmed or configured to deliver fluid to a patient;
determining, with the at least one first injection system, a first subset of the plurality of injection control data sets according to which the at least one first injection system is configured to control delivery of at least one fluid to the patient;
providing, at the at least one first injection system, the first subset of the plurality of injection control data sets for selection of an injection control data set for use in delivering the at least one fluid to the patient with the at least one first injection system;
modifying, with the at least one first injection system, the parameters of one or more injection control data sets of the plurality of injection control data sets, wherein the one or more injection control data sets are associated with a unique identifier associated with the at least one third injection system;
in response to modifying the parameters of the one or more injection control data sets, with the at least one first injection system, storing the modified one or more injection control data sets including the modified parameters and deleting the one or more injection control data sets; and
transmitting, with the at least one first injection system, the plurality of unique identifiers and the plurality of injection control data sets including the modified one or more injection control data sets to the at least one second injection system,
wherein the at least one first injection system includes a first type of injection system, wherein the at least one second injection system includes a second type of injection system, and wherein the first type of injection system is different than the second type of injection system, wherein the at least one first injection system is configured to control delivery of the at least one fluid to the patient based on the first subset of the plurality of injection control data sets, wherein the at least one second injection system is configured to control delivery of one or more fluids to the patient based on a second subset of the plurality of injection control data sets, wherein the second subset includes at least one injection control data set different than the first subset, wherein the at least one first injection system cannot execute the at least one different injection control data set to control delivery of the at least one fluid to the patient based on the at least one different injection control data set, and wherein the at least one first injection system stores, in a data storage device local to the at least one first injection system, each injection control data set of the plurality of the injection control data sets including the at least one different injection control data set that the at least one first injection system cannot execute to control delivery of the at least one fluid to the patient.

2. The computer-implemented method of claim 1, further comprising:
providing, with the at least one first injection system, the first subset of the plurality of injection control data sets to a user without providing a remainder of the plurality of injection control data sets to the user;
receiving, with the at least one first injection system, user input;
determining, with the at least one first injection system, a selected injection control data set for delivering the at least one fluid to the patient from the first subset of the plurality of injection control data sets based on the user input; and
controlling, with the at least one first injection system, delivery of the at least one fluid to the patient according to the selected injection control data set.

3. The computer-implemented method of claim 1, further comprising:
determining, with the at least one second injection system, the second subset of the plurality of injection control data sets according to which the at least one second injection system is configured to control delivery of the one or more fluids to the patient; and providing, with the at least one second injection system, the second subset of the plurality of injection control data sets for selection of an injection control data set for use in delivering the one or more fluids to the patient with the at least one second injection system.

4. The computer-implemented method of claim 3, further comprising:

providing, with the at least one second injection system, the second subset of the plurality of injection control data sets to a user without providing a remainder of the plurality of injection control data sets to the user;

receiving, with the at least one second injection system, user input;

determining, with the at least one second injection system, a selected injection control data set for use in delivering the one or more fluids to the patient from the second subset of the plurality of injection control data sets based on the user input; and controlling, with the at least one second injection system, delivery of the one or more fluids to the patient according to the selected injection control data set.

5. The computer-implemented method of claim 1, wherein the plurality of injection control data sets includes a plurality of injection protocols, the method further comprising:

receiving, with the at least one first injection system, a selection of an injection protocol from the first subset for use in delivering the at least one fluid to the patient with the at least one first injection system; and delivering, with the at least one first injection system, the at least one fluid to the patient according to the selected injection protocol.

6. The computer-implemented method of claim 1, wherein the plurality of injection control data sets includes a plurality of presets, the method further comprising:

receiving, with the at least one first injection system, a selection of a preset from the first subset for use in delivering the at least one fluid to the patient with the at least one first injection system;

receiving, with the at least one first injection system, patient data associated with the patient and procedure data associated with a procedure to be performed on the patient;

determining, with the at least one first injection system, an injection protocol for use in delivering the at least one fluid to the patient with the at least one first injection system based on the selected preset, the patient data, and the procedure data; and delivering, with the at least one first injection system, the at least one fluid to the patient according to the determined injection protocol.

7. The computer-implemented method of claim 1, further comprising:

receiving, with the at least one first injection system, at least one of (i) accessory data associated with a plurality of catheters and (ii) fluid data associated with a plurality of fluids;

receiving, with the at least one first injection system, a selection of the injection control data set from the first subset for use in delivering the at least one fluid to the patient with the at least one injection system;

determining, with the at least one first injection system, at least one of (i) a subset of the plurality of catheters for use in delivering the at least one fluid to the patient and (ii) a subset of the plurality of fluids for use in delivering the at least one fluid to the patient, based on the selected injection control data set; and providing, with the at least one first injection system, the at least one of (i) the subset of the plurality of catheters, for selection of a catheter for use in delivering the at least one fluid to the patient, and (ii) the subset of the plurality of fluids, for selection of a fluid for use in delivering the at least one fluid to the patient.

8. A peer exchange data management system comprising:

at least one first injection system configured to control delivery of at least one fluid to a patient, wherein the at least one first injection system includes at least one processor programmed or configured to:

store a plurality of unique identifiers associated with a plurality of injection systems including the at least one first injection system, at least one second injection system, and at least one third injection system, wherein the plurality of injection systems includes a peer-to-peer network of injection systems formed by the plurality of injection systems implementing a virtual overlay network on top of a physical network topology;

store a plurality of injection control data sets, wherein each unique identifier is associated with at least one injection control data set of the plurality of injection control data sets including parameters according to which an injection system associated with the unique identifier is configured to be programmed or configured to deliver fluid to a patient;

determine a first subset of the plurality of injection control data sets according to which the at least one first injection system is configured to control delivery of the at least one fluid to the patient;

provide the first subset of the plurality of injection control data sets for selection of an injection control data set for use in delivering the at least one fluid to the patient with the at least one first injection system;

modify the parameters of one or more injection control data sets of the plurality of injection control data sets, wherein the one or more injection control data sets are associated with a unique identifier associated with the at least one third injection system;

in response to modifying the parameters of the one or more injection control data sets, store the modified one or more injection control data sets including the modified parameters and delete the existing one or more injection control data sets; and transmit the plurality of unique identifiers and the plurality of injection control data sets including the modified one or more injection control data sets to the at least one second injection system, wherein the at least one first injection system includes a first type of injection system, wherein the at least one second injection system includes a second type of injection system, and wherein the first type of injection system is different than the second type of injection system, wherein the at least one first injection system is configured to control delivery of the at least one fluid to the patient based on the first subset of the plurality of injection control data sets, wherein the at least one second injection system is configured to control delivery of one or more fluids to the patient based on a second subset of the plurality of injection control data sets, wherein the second subset includes at least one injection control data set different than the first subset, wherein the at least one first injection system cannot execute the at least one different injection control data set to control delivery of the at least one fluid to the patient based on the at least one different injection control data set, and wherein the at least one first injection system stores, in a data storage device local to the at least one first injection system, each injection control data set of the plurality of the injection control data sets including the at least one different injection control data set that the at least one first injection system cannot execute to control delivery of the at least one fluid to the patient.

9. The system of claim 8, wherein the at least one first injection system is further programmed or configured to:
provide the first subset of the plurality of injection control data sets to a user without providing a remainder of the plurality of injection control data sets to the user;
receive user input;
determine a selected injection control data set for delivering the at least one fluid to the patient from the first subset of the plurality of injection control data sets based on the user input; and
control delivery of the at least one fluid to the patient according to the selected injection control data set.

10. The system of claim 8, further comprising:
the at least one second injection system configured to deliver the one or more fluids to the patient, wherein the at least one second injection system includes at least one processor programmed or configured to:
determine the second subset of the plurality of injection control data sets according to which the at least one second injection system is configured to control delivery of the one or more fluids to the patient; and
provide the second subset of the plurality of injection control data sets for selection of an injection control data set for use in delivering the one or more fluids to the patient with the at least one second injection system.

11. The system of claim 10, wherein the at least one second injection system is further programmed or configured to:
provide the second subset of the plurality of injection control data sets to a user without providing a remainder of the plurality of injection control data sets to the user;
receive user input;
determine a selected injection control data set for use in delivering the one or more fluids to the patient from the second subset of the plurality of injection control data sets based on the user input; and
control delivery of the one or more fluids to the patient according to the selected injection control data set.

12. The system of claim 8, wherein the plurality of injection control data sets includes a plurality of injection protocols, and wherein the at least one first injection system is further programmed or configured to:
receive a selection of an injection protocol from the first subset or use in delivering the at least one fluid to the patient with the at least one first injection system; and
deliver the at least one fluid to the patient according to the selected injection protocol.

13. The system of claim 8, wherein the plurality of injection control data sets includes a plurality of presets, and wherein the at least one first injection system is further programmed or configured to:
receive a selection of a preset from the first subset or use in delivering the at least one fluid to the patient with the at least one first injection system;
receive patient data associated with the patient and procedure data associated with a procedure to be performed on the patient;
determine an injection protocol for use in delivering the at least one fluid to the patient with the at least one first injection system based on the selected preset, the patient data, and the procedure data; and
deliver the at least one fluid to the patient according to the determined injection protocol.

14. The system of claim 8, wherein the at least one first injection system is further programmed or configured to:
receive at least one of (i) accessory data associated with a plurality of catheters and (ii) fluid data associated with a plurality of fluids;
receive a selection of the injection control data set from the first subset or use in delivering the at least one fluid to the patient with the at least one injection system;
determine at least one of (i) a subset of the plurality of catheters for use in delivering the at least one fluid to the patient and (ii) a subset of the plurality of fluids for use in delivering the at least one fluid to the patient, based on the selected injection control data set; and
provide the at least one of (i) the subset of the plurality of catheters, for selection of a catheter for use in delivering the at least one fluid to the patient, and (ii) the subset of the plurality of fluids, for selection of a fluid for use in delivering the at least one fluid to the patient.

15. A computer program product for peer exchange of data between injection systems, the computer program product comprising at least one non-transitory computer-readable medium comprising one or more instructions that, when executed by at least one processor, cause the at least one processor to:
store, in at least one first injection system, a plurality of unique identifiers associated with a plurality of injection systems including the at least one first injection system, at least one second injection system, and at least one third injection system, wherein the plurality of injection systems includes a peer-to-peer network of injection systems formed by the plurality of injection systems implementing a virtual overlay network on top of a physical network topology;
store a plurality of injection control data sets in the at least one first injection system, wherein each unique identifier is associated with at least one injection control data set of the plurality of injection control data sets including parameters according to which an injection system associated with the unique identifier is configured to be programmed or configured to deliver fluid to a patient;
determine a first subset of the plurality of injection control data sets according to which the at least one first injection system is configured to control delivery of at least one fluid to the patient;
provide, at the at least one first injection system, the first subset of the plurality of injection control data sets for selection of an injection control data set for use in delivering the at least one fluid to the patient with the at least one first injection system;
modify, at the at least one first injection system, the parameters of one or more injection control data sets of the plurality of injection control data sets, wherein the one or more injection control data sets are associated with a unique identifier associated with the at least one third injection system;
in response to modifying the parameters of the one or more injection control data sets, store the modified one or more injection control data sets including the modified parameters and delete the existing one or more injection control data sets; and transmit the plurality of unique identifiers and the plurality of injection control data sets including the modified one or more injection control data sets from the at least one first injection system to the at least one second injection system, wherein the at least one first injection system includes a first type of injection system, wherein the at least one second injection system includes a second type of injection system, and wherein the first type of injection system is different than the second type of injection system, wherein the at least one first injection system is configured to control delivery of the at least one fluid to the patient based on the first subset of the plurality of injection control data sets, wherein the at least one second injection system is configured to control delivery of the one or more fluids to the patient based on a second subset of the plurality of injection control data sets, wherein the second subset includes at least one injection control data set different than the first subset, wherein the at least one first injection system cannot execute the at least one different injection control data set to control delivery of the at least one fluid to the patient based on the at least one different injection control data set, and wherein the at least one first injection system stores, in a data storage device local to the at least one first injection system, each injection control data set of the plurality of the injection control data sets including the at least one different injection control data set that the at least one first injection system cannot execute to control delivery of the at least one fluid to the patient.

16. The computer-implemented method of claim 1, wherein each of the plurality of injection systems stores, in a data storage device local to the injection system, each of the plurality of the injection control data sets for the plurality of injection systems.

* * * * *

UNITED STATES PATENT AND TRADEMARK OFFICE
CERTIFICATE OF CORRECTION

PATENT NO. : 11,430,558 B2
APPLICATION NO. : 16/621018
DATED : August 30, 2022
INVENTOR(S) : Volkar et al.

It is certified that error appears in the above-identified patent and that said Letters Patent is hereby corrected as shown below:

In the Specification
In Column 1, Line 59, delete "unavailable;" and insert -- unavailable, --, therefor.
In Column 1, Lines 66-67, delete "efficient; secure;" and insert -- efficient, secure, --, therefor.
In Column 2, Line 20, delete "system;" and insert -- system, --, therefor.
In Column 3, Line 25, delete "system;" and insert -- system, --, therefor.
In Column 3, Line 45, delete "presets;" and insert -- presets, --, therefor.
In Column 5, Line 12, delete "aspects;" and insert -- aspects, --, therefor.
In Column 7, Line 31, delete "aspects;" and insert -- aspects, --, therefor.
In Column 7, Line 37, delete "system;" and insert -- system, --, therefor.
In Column 8, Line 6, delete "sets;" and insert -- sets, --, therefor.
In Column 8, Line 56, delete "exam;" and insert -- exam, --, therefor.
In Column 9, Line 1, delete "system;" and insert -- system, --, therefor.
In Column 9, Line 33, delete "transmitting;" and insert -- transmitting, --, therefor.
In Column 9, Line 67, delete "system;" and insert -- system, --, therefor.
In Column 10, Line 1, delete "determining;" and insert -- determining, --, therefor.
In Column 10, Line 14, delete "providing;" and insert -- providing, --, therefor.
In Column 10, Line 20, delete "system;" and insert -- system, --, therefor.
In Column 10, Line 23, delete "controlling;" and insert -- controlling, --, therefor.
In Column 10, Line 46, delete "providing;" and insert -- providing, --, therefor.
In Column 10, Line 47, delete "system;" and insert -- system, --, therefor.
In Column 10, Line 53, delete "providing;" and insert -- providing, --, therefor.
In Column 10, Line 62, delete "input:" and insert -- input; --, therefor.
In Column 11, Line 34, delete "system:" and insert -- system; --, therefor.
In Column 12, Line 21, delete "Clause 14," and insert -- Clause 14. --, therefor.
In Column 12, Line 31, delete "Clause 15," and insert -- Clause 15. --, therefor.
In Column 13, Line 4, delete "protocols;" and insert -- protocols, --, therefor.
In Column 15, Line 25, delete "system;" and insert -- system, --, therefor.
In Column 15, Line 53, delete "Clause 34," and insert -- Clause 34. --, therefor.
In Column 16, Line 4, delete "Clause 36," and insert -- Clause 36. --, therefor.
In Column 16, Line 49, delete "Clause 39," and insert -- Clause 39. --, therefor.

Signed and Sealed this
Sixth Day of December, 2022

*Katherine Kelly Vidal*

Katherine Kelly Vidal
*Director of the United States Patent and Trademark Office*

CERTIFICATE OF CORRECTION (continued)
U.S. Pat. No. 11,430,558 B2

In Column 16, Line 56, delete "system;" and insert -- system, --, therefor.
In Column 20, Line 40, delete "location;" and insert -- location, --, therefor.
In Column 21, Line 19, delete "FIG. 10" and insert -- FIG. 1C --, therefor.
In Column 23, Line 29, delete "saline)." and insert -- saline. --, therefor.
In Column 23, Line 39, delete "example;" and insert -- example, --, therefor.
In Column 24, Line 4, delete "protocol;" and insert -- protocol, --, therefor.
In Column 24, Line 16, delete "preset data; patient data;" and insert -- preset data, patient data, --, therefor.
In Column 24, Line 21, delete "patient;" and insert -- patient, --, therefor.
In Column 24, Line 22, delete "patient;" and insert -- patient, --, therefor.
In Column 24, Line 27, delete "aspects;" and insert -- aspects, --, therefor.
In Column 24, Line 38, delete "(e.g.;" and insert -- (e.g., --, therefor.
In Column 24, Line 45, delete "name;" and insert -- name, --, therefor.
In Column 24, Line 47, delete "system;" and insert -- system, --, therefor.
In Column 24, Line 52, delete "aspects;" and insert -- aspects, --, therefor.
In Column 24, Line 55, delete "(e.g.;" and insert -- (e.g., --, therefor.
In Column 24, Line 57, delete "thereof;" and insert -- thereof, --, therefor.
In Column 24, Line 63, delete "system;" and insert -- system, --, therefor.
In Column 24, Line 67, delete "(e.g.;" and insert -- (e.g., --, therefor.
In Column 25, Line 58, delete "YIN," and insert -- Y/N, --, therefor.
In Column 26, Line 43, delete "(Ply)" and insert -- (PIV) --, therefor.
In Column 27, Line 3, delete "etc.)," and insert -- etc.). --, therefor.
In Column 27, Line 52, delete "FIGS. 1A-1E," and insert -- FIGS. 1A-1E. --, therefor.
In Column 29, Line 10, delete "herein," and insert -- herein. --, therefor.
In Column 31, Line 31, delete "patient;" and insert -- patient, --, therefor.
In Column 31, Line 47, delete "etc.;" and insert -- etc., --, therefor.
In Column 31, Line 66, delete "eta)" and insert -- etc.) --, therefor.
In Column 32, Line 34, delete "sets;" and insert -- sets, --, therefor.
In Column 32, Line 40, delete "installed; initiated;" and insert -- installed, initiated, --, therefor.
In Column 32, Line 49, delete "protocol;" and insert -- protocol, --, therefor.
In Column 32, Line 50, delete "subset;" and insert -- subset, --, therefor.
In Column 32, Line 63, delete "102b;" and insert -- 102b, --, therefor.
In Column 33, Line 63, delete "second injection system 102a" and insert -- second injection system 102b --, therefor.
In Column 34, Lines 2-3, delete "second injection system 102a" and insert -- second injection system 102b --, therefor.
In Column 34, Line 45, delete "eta)" and insert -- etc.) --, therefor.
In Column 35, Line 28, delete "In-some" and insert -- In some --, therefor.
In Column 37, Line 65, delete "eta)." and insert -- etc.). --, therefor.
In Column 40, Line 62, delete "exam;" and insert -- exam, --, therefor.
In Column 41, Line 7, delete "system;" and insert -- system, --, therefor.
In Column 41, Line 38, delete "(e.g.;" and insert -- (e.g., --, therefor.